(12) United States Patent
Gasperino et al.

(10) Patent No.: US 9,625,385 B2
(45) Date of Patent: Apr. 18, 2017

(54) PHOTOTHERMAL SPECTROSCOPY SYSTEMS FOR OFFSET SYNCHRONOUS TESTING OF FLOW ASSAYS AND METHODS OF USING SAME

(71) Applicant: Tokitae LLC, Bellevue, WA (US)

(72) Inventors: David Gasperino, Lake Forest Park, WA (US); Matthew P. Horning, Redmond, WA (US); Kevin Paul Flood Nichols, Issaquah, WA (US); Phil Rutschman, Seattle, WA (US); Benjamin K. Wilson, Kirkland, WA (US); Ozgur Emek Yildirim, Bellevue, WA (US)

(73) Assignee: TOKITAE LLC, Bellevue, WA (US)

( * ) Notice: Subject to any disclaimer, the term of this patent is extended or adjusted under 35 U.S.C. 154(b) by 0 days.

(21) Appl. No.: 14/630,489

(22) Filed: Feb. 24, 2015

(65) Prior Publication Data

US 2016/0245748 A1 Aug. 25, 2016

(51) Int. Cl.
*G01J 5/02* (2006.01)
*G01N 21/63* (2006.01)
*G01N 33/543* (2006.01)
*G01N 21/17* (2006.01)

(52) U.S. Cl.
CPC .......... *G01N 21/63* (2013.01); *G01N 21/171* (2013.01); *G01N 33/54373* (2013.01); *G01N 2021/1714* (2013.01); *G01N 2201/0697* (2013.01)

(58) Field of Classification Search
CPC .... G01N 25/72; G01N 29/348; G01N 29/228; G01N 21/71; G01N 29/346
See application file for complete search history.

(56) References Cited

U.S. PATENT DOCUMENTS

| 7,262,414 | B1 | 8/2007 | Carrieri et al. | |
|---|---|---|---|---|
| 2008/0018890 | A1* | 1/2008 | Maity | G01J 1/44 356/301 |
| 2010/0135857 | A1* | 6/2010 | Hunter | G01N 21/6428 422/82.08 |
| 2012/0061587 | A1* | 3/2012 | Wu | G01N 21/6458 250/459.1 |
| 2014/0170674 | A1* | 6/2014 | He | G01N 33/558 435/7.4 |
| 2014/0377770 | A1* | 12/2014 | Bischof | G01N 21/8483 435/7.1 |
| 2015/0036145 | A1 | 2/2015 | Cichos et al. | |

FOREIGN PATENT DOCUMENTS

WO  WO 2013/116333  8/2013
WO  WO 2013/186735 A2  12/2013

OTHER PUBLICATIONS

U.S. Appl. No. 14/604,396, Horning et al.
(Continued)

*Primary Examiner* — David Porta
*Assistant Examiner* — Mamadou Faye
(74) *Attorney, Agent, or Firm* — Dorsey & Whitney LLP

(57) ABSTRACT

Embodiments disclosed herein are directed to photothermal spectroscopy apparatuses and systems for offset synchronous testing of flow assays. Methods of using and operating such photothermal spectroscopy systems are also disclosed.

48 Claims, 14 Drawing Sheets

(56) References Cited

OTHER PUBLICATIONS

PCT International Search Report; International App. No. PCT/US2016/013883; Apr. 14, 2016; pp. 1-3.
PCT International Search Report; International App. No. PCT/US2016/017678; May 11, 2016; pp. 1-3.
Dell et al.; "Towards a Point-of-Care Diagnostic System: Automated Analysis of Immunoassay Test Data on a Cell Phone"; NSDR; Jun. 28, 2011; pp. 3-8; ACM.
Honda et al.; "Nanoscale heating of laser irradiated single gold nanoparticles in liquid"; Optics Express; Jun. 20, 2011; pp. 12375-12383; vol. 19, No. 13; Optical Society of America.
NanoAct; "Development using NanoAct Cellulose Nanobeads"; printed on Oct. 2, 2016; 2 pages; located at: http://www.dcndx.com/service-detail/development-using-nanoact-cellulose-nanobeads.
Qin et al.; "Significantly Improved Analytical Sensitivity of Lateral Flow Immunoassays by Thermal Contrast"; National Institute of Health; Apr. 27, 2012; pp. 1-9; vol. 51, No. 18; Angew Chemical International Edition England.

\* cited by examiner

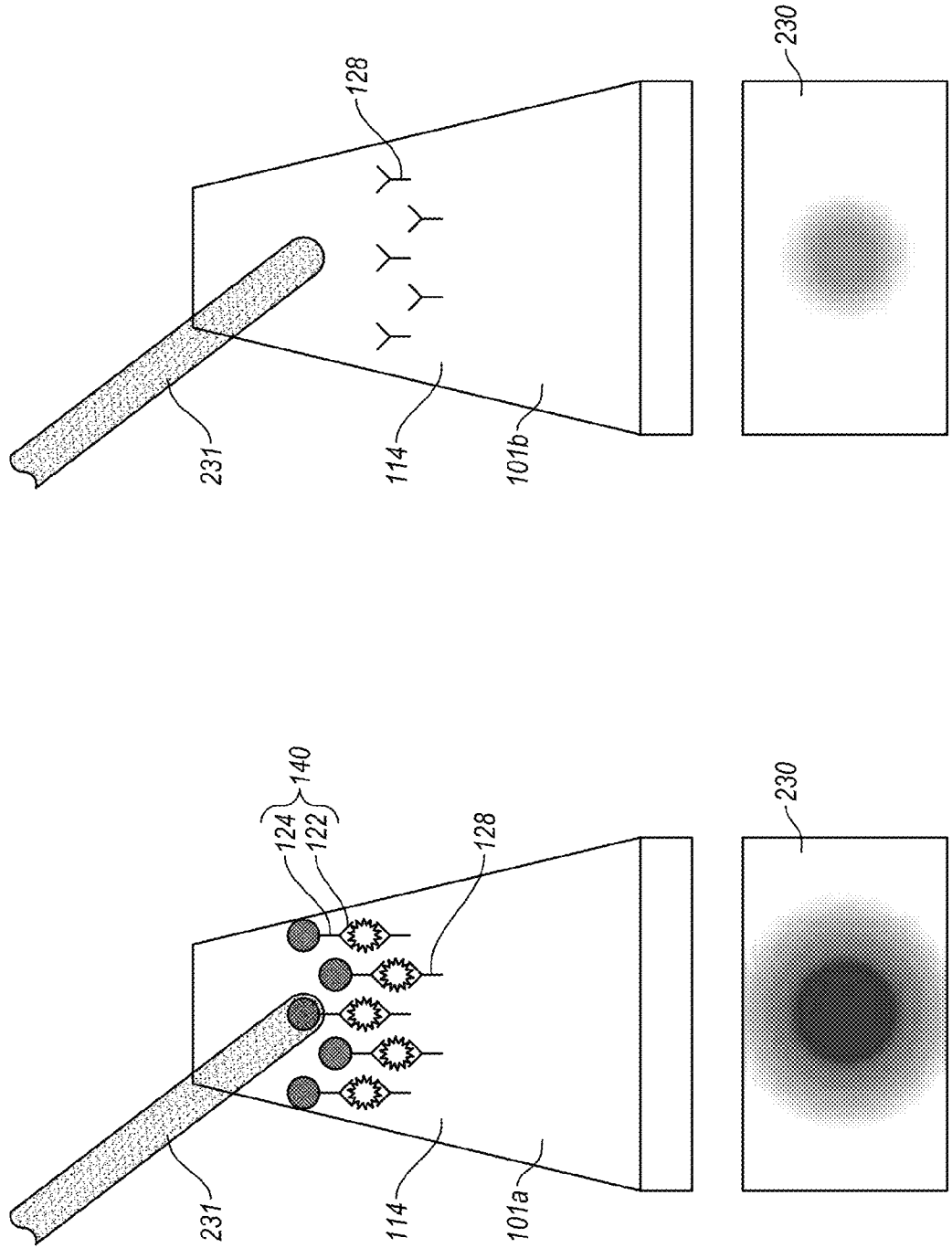

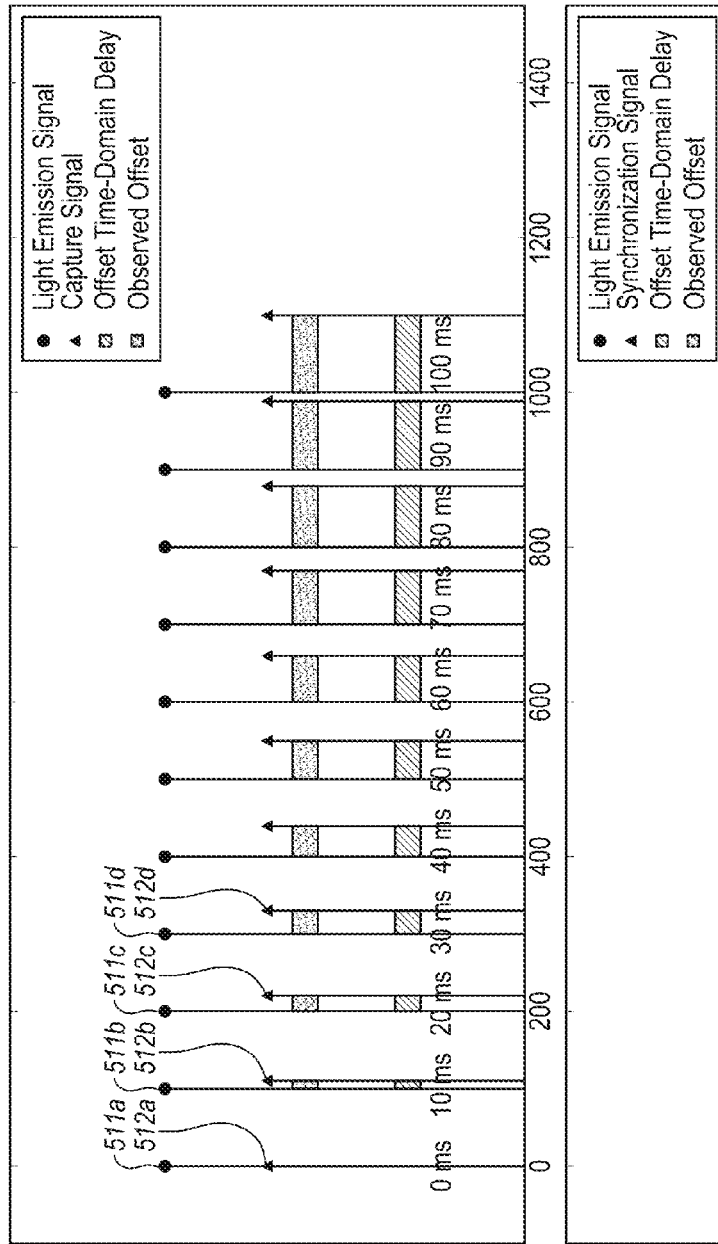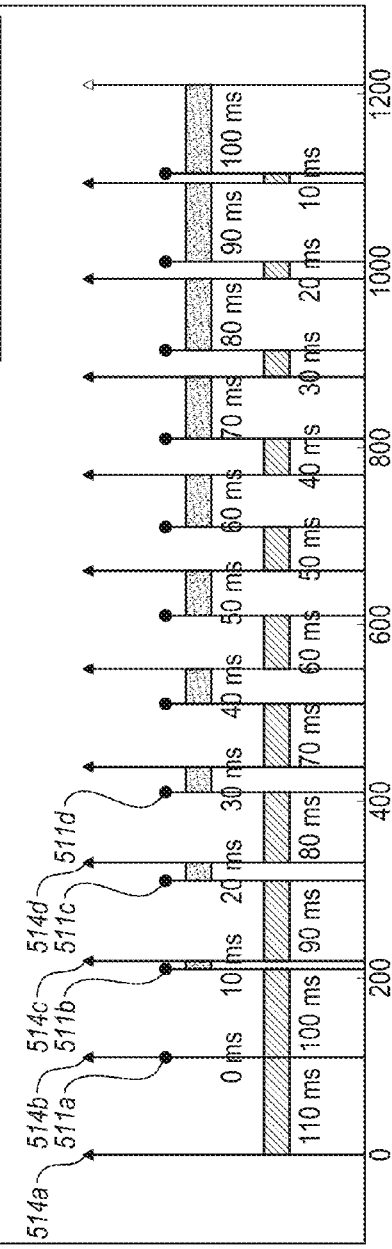

PHOTOTHERMAL SPECTROSCOPY SYSTEMS FOR OFFSET SYNCHRONOUS TESTING OF FLOW ASSAYS AND METHODS OF USING SAME

If an Application Data Sheet (ADS) has been filed on the filing date of this application, it is incorporated by reference herein. Any applications claimed on the ADS for priority under 35 U.S.C. §§119, 120, 121, or 365(c), and any and all parent, grandparent, great-grandparent, etc. applications of such applications, are also incorporated by reference, including any priority claims made in those applications and any material incorporated by reference, to the extent such subject matter is not inconsistent herewith.

CROSS-REFERENCE TO RELATED APPLICATIONS

The present application claims the benefit of the earliest available effective filing date(s) from the following listed application(s) (the "Priority Applications"), if any, listed below (e.g., claims earliest available priority dates for other than provisional patent applications or claims benefits under 35 USC §119(e) for provisional patent applications, for any and all parent, grandparent, great-grandparent, etc. applications of the Priority Application(s)).

PRIORITY APPLICATIONS

None.

If the listings of applications provided above are inconsistent with the listings provided via an ADS, it is the intent of the Applicant to claim priority to each application that appears in the Domestic Benefit/National Stage Information section of the ADS and to each application that appears in the Priority Applications section of this application.

All subject matter of the Priority Applications and of any and all applications related to the Priority Applications by priority claims (directly or indirectly), including any priority claims made and subject matter incorporated by reference therein as of the filing date of the instant application, is incorporated herein by reference to the extent such subject matter is not inconsistent herewith.

BACKGROUND

A lateral flow assay (LFA) can be a paper-based device that detects a presence of an analyte in a sample. LFAs are a common point of care diagnostic tool. LFAs function by wicking (e.g., capillary action) a sample of interest through a porous membrane (e.g. paper) where chemical reactions can occur in and on the surface of the porous membrane. The LFA can contain a conjugate material therein. Conjugate materials are typically formulated to provide the solvent(s) and reactant(s) necessary to dissolve, react, color, tag, or bond to the suspected analyte in a sample. Thus, if the analyte is present, the conjugate or a component thereof will react with the analyte in the sample. The conjugate material can include an indicator material configured to provide indication of a presence of the analyte, a reacted analyte, or an analyte-conjugate complex. Typically, the readout of an LFA can be a visual change at some point along a length of the LFA. Many LFAs include an analyte collection material near the distal end of the LFA whereby the analyte and any indicator particle bonded thereto are bound in large concentration to provide visual or other indication of a positive or negative result.

Systems incorporating photothermal spectroscopy assay readers can enhance the sensitivity of LFA and similar assay results beyond visual detection. A photothermal spectroscopy assay reader can detect radiation of heat from the surface of an LFA saturated with the sample of interest. The conjugate material reacted with analyte in the sample can absorb energy from the light. The photothermal spectroscopy assay reader can detect a thermal response from the irradiated conjugate material on the surface of the LFA, which can provide an indication of the presence of the analyte.

Manufacturers and users of photothermal spectroscopy assay readers and LFAs continue to seek photothermal spectroscopy assay readers and LFAs with improved detection capability.

SUMMARY

Embodiments disclosed herein are directed to photothermal spectroscopy apparatuses and systems for offset synchronous testing of flow assays. Methods of using and operating such photothermal spectroscopy systems are also disclosed.

In an embodiment, a system for detecting a presence of an analyte in a sample disposed in a flow assay having optically-absorbing indicator particles therein is disclosed. The system includes a light source positioned and configured to irradiate at least a portion of the flow assay and the optically-absorbing indicator particles therein. The system further includes a photothermal spectroscopy assay reader configured to capture a plurality of thermal signals of the flow assay including the optically-absorbing indicator particles. The system additionally includes a control system including control electrical circuitry operably coupled to the light source and the photothermal spectroscopy assay reader. The control electrical circuitry is configured to synchronize operation of the light source and the photothermal spectroscopy assay reader at progressively offset time intervals.

In an embodiment, a method of detecting a presence of an analyte in a sample is disclosed. The method includes providing a flow assay including a plurality of optically-absorbing indicator particles therein to a carriage of a detection apparatus. The method also includes initiating operation of a detection apparatus, which includes a light source and a photothermal spectroscopy assay reader configured to capture a plurality of thermal signals of the flow assay including the plurality of optically-absorbing indicator particles therein. The method further includes emitting a plurality of pulses of light from the light source onto at least a portion of the flow assay. The method additionally includes substantially synchronizing capture of a plurality of thermal signals in progressively offset time-domain intervals, with the plurality of thermal signals being of the at least a portion of the flow assay irradiated with the plurality of pulses of light. The method includes capturing one or more of the plurality of thermal signals of the at least a portion of the flow assay irradiated with the plurality of pulses of light. The method further includes determining the presence of the analyte in the sample based at least partially on the plurality of thermal signals.

Features from any of the disclosed embodiments can be used in combination with one another, without limitation. In addition, other features and advantages of the present disclosure will become apparent to those of ordinary skill in the art through consideration of the following detailed description and the accompanying drawings.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIGS. 2A and 2B are schematic representations of the photothermal response of respective LFAs when analyte bound to optically-absorbing indicator particles is present and absent, respectively.

FIG. 7A is a graphical representation of the progressive time-domain delay between signals from a system for detecting the presence of an analyte in a sample according to an embodiment.

FIG. 7B is a graphical representation of the progressive time-domain delay between signals from a system for detecting the presence of an analyte in a sample according to an embodiment.

DETAILED DESCRIPTION

Figure 1A:
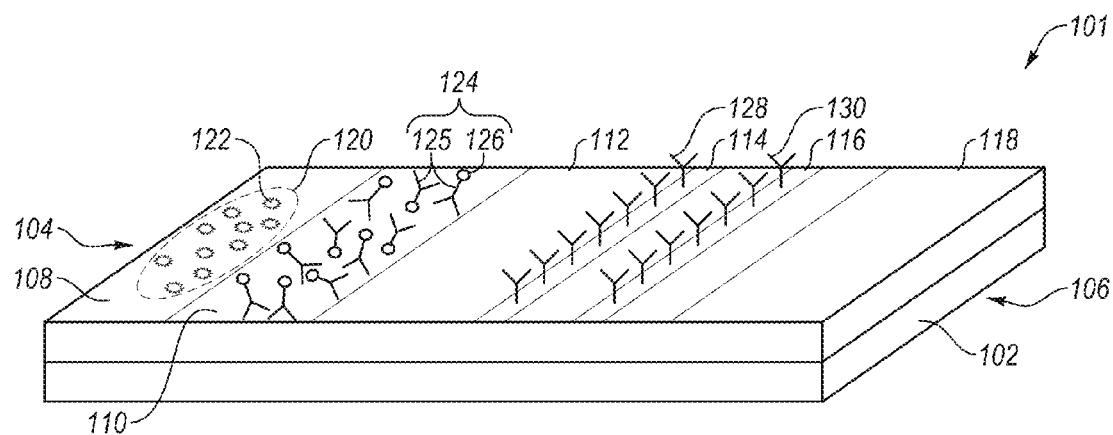
FIGS. 1A-1C are isometric views of a lateral flow assay during use according to an embodiment, which can be read by any of embodiments of photothermal spectroscopy systems disclosed herein.

Embodiments disclosed herein are directed to photothermal spectroscopy systems for offset synchronous testing of flow assays (e.g., a LFA). Methods of operating and using such photothermal spectroscopy systems are also disclosed.

A LFA can be used to provide point of care testing for a variety of purposes, such as drug tests, pregnancy tests, fertility tests, and tests for infectious agents such as influenza virus, hepatitis virus and human immunodeficiency virus (HIV), by way of non-limiting examples. LFAs and similar flow assays function by moving a sample including an analyte therein through a length of a capillary bed via capillary action. During capillary transport, the analyte in the sample is exposed to a conjugate material configured to react with the analyte to aid in detection thereof. The conjugate can contain indicator particles (e.g., optically-absorbing indicator particles, taggant, or color molecules) therein. The indicator particles are bound to a conjugate molecule or otherwise configured to react with the analyte, reacted analyte molecule, or analyte-conjugate complex and provide a visual or other indication thereof when concentrated (e.g., bound to an indication strip) in large numbers. Detection of the analyte can depend on the absence or presence of large enough numbers of the analyte to provide a discernable visual indication thereof. However, during the early stages of an infection, an analyte may not be present in the system of an infected subject in sufficient numbers to be visually detectable by an assay.

A system for detecting the presence of an analyte in a sample can use the thermal signature of optically-absorbing indicator particles (e.g., the taggant molecule or a portion thereof such as a gold nanoparticle) bound to an analyte to determine if the analyte is present in a sample. A light source can irradiate a portion of an LFA and thereby raise the temperature of any optically-absorbing indicator particles therein. A thermal detector, such as a photothermal spectroscopy assay reader, can measure the portion of the LFA irradiated with light and determine the temperature of the portion of the LFA for a point in time at which the measurement was captured. Indicator particles that are strong optical and/or thermal absorbers, such as gold nanoparticles, will absorb more radiation from a light source than other materials in the LFA. Much of this absorbed energy is converted into heat, which causes an increase in the infrared radiation from the indicator particles and surrounding materials, which will show more readily on a thermal measurement, such as a photothermal spectrograph, than those portions not having optically-absorbing indicator particles therein. Similarly, a portion of a LFA having a higher concentration of optically-absorbing indicator particles therein will generate more heat upon optical excitation and have a different thermal signature than a portion of a flow assay having a lower concentration of optically-absorbing indicator particles therein. A series of thermal signals (e.g., temperature measurements, photothermal spectrographic images, or infrared images) can be measured at sequentially offset time-domain intervals or delays from the time of irradiation from the light source can be used to determine an ideal capture time for a thermal signal. The ideal capture time provides the instant in time that greatest change in temperature per change in time is located for a given analyte and where in time (as spaced from irradiation of the sample) a sample should be tested to provide the highest sensitivity for detecting the analyte.

A system suitable for such measurements includes a light source, a photothermal spectroscopy assay reader and a control system for substantially synchronizing the time relationship between a series of irradiations by the light source and capture of thermal signals by the photothermal spectroscopy assay reader. Based on the series of thermal signals, such as those captured in each progressively time-delayed from each of a series of irradiations by the light source, a curve of change in temperature per change in time versus time can be built to show the ideal detection time. Samples can be tested at the ideal detection time to provide the greatest sensitivity to the analyte bound to the optically-absorbing particles so that early detection can be achieved.

Figure 1B:
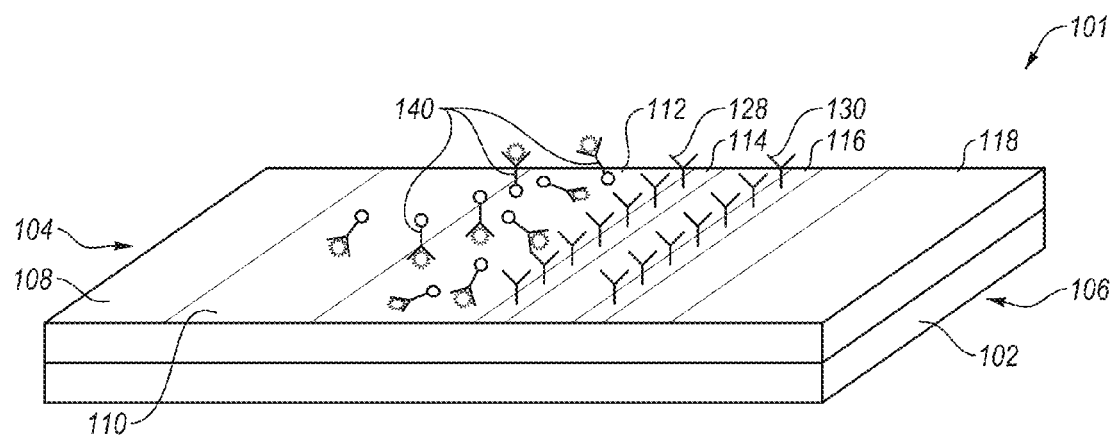
Figure 1C:
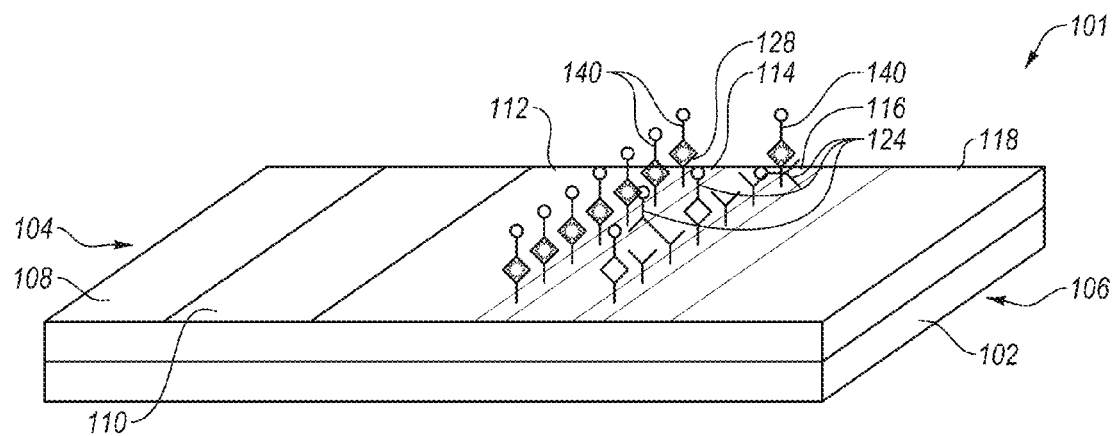

FIGS. 1A-1C depict an embodiment of a LFA 101 during use at respectively different points in time that can be read by any of the embodiments of photothermal spectroscopy systems disclosed herein. It is noted that that any of the embodiments of photothermal spectroscopy systems disclosed herein can read flow assays having different configurations and the LFA 101 shown in FIGS. 1A-1C is merely an example of a suitable flow assay. The LFA 101 includes a backing layer 102 having a first end 104 and a second end 106. The backing layer 102 supports a sample pad 108 adjacent to the first end 104, a conjugate pad 110, a membrane 112 having a test line 114 and a control line 116, and a wicking pad 118 adjacent to the second end 106. A sample 120, possibly having an analyte 122 therein, can be applied to the sample pad 108, wherein the sample travels from the first end 104 through the sample pad 108, conjugate pad 116, and membrane 112, to the wicking pad 118 at the second end 106 via capillary action. Any analyte 122 in the sample 120 can bond to a conjugate material 124, including any indicator particles therein are carried to the membrane 112, wherein the conjugate-analyte complex is collected on the test line 114 via interaction with one or more of a plurality of capture molecules 128 (e.g., antibodies or other molecules capable of retaining one or more of the analyte, the conjugate, or the indicator particles) in the test line 114. Some of the analyte 122, analyte-conjugate complex, conjugate molecules, or other material in the sample 120 can pass the test line 114 and be bound to a control line 116 via one or more of a plurality of control molecules 130 which are configured to capture one or more of the analyte 122, analyte-conjugate complex, conjugate molecules, or other material in the sample to provide a visible indication of the efficacy of the test.

Referring to FIG. 1A, in an embodiment at a first point in time, a sample 120 can include any substance or fluid capable of carrying a suspected analyte 122 (e.g., dispersion, emulsion, etc.) such as diluted or undiluted blood, serum, urine, saliva, mucus, or other samples from a test subject. The sample 120, including any analyte 122 therein is applied to the sample pad 106 via pipette, dropper, pouring, dipping, or other any suitable technique. The sample 120 is carried from the first end 104 toward the second end 106 via capillary action. The sample 120 first passes through the conjugate pad 110.

The conjugate pad 110 includes a conjugate material 124 in at least a portion thereof (e.g., embedded or otherwise dispersed therein). The conjugate material 124 can be formulated to react with a specific analyte (e.g., antigen, molecule, etc.) to yield a specific analyte-conjugate complex or molecule. Typical conjugate materials can include chemical reactants, antibodies 125, bio-active agents, sugars, salts, indicator particles 126 (e.g., latex, colloidal gold, nanobeads, or other suitable molecules) which can include optically-absorbing indicator particles, and other materials formulated to ensure satisfactory reaction or bonding between the analyte and one or more conjugate components or indicator particles. For example, the analyte 122 can be a virus or antigen and the conjugate material 124 can contain the antibody 125 to the virus or antigen, the antibody can have a optically-absorbing indicator particle 126 bonded thereto. Optically-absorbing indicator particles for use with embodiments of photothermal spectroscopy systems disclosed herein absorb electromagnetic energy, e.g., light energy, and subsequently emit thermal energy, e.g. heat. Suitable wavelengths of electromagnetic radiation can include one or more of visible light, infrared radiation, ultraviolet radiation, microwave radiation, or any other electromagnetic radiation capable of delivering thermal energy, including both visible and non-visible wavelengths. Suitable optically-absorbing indicator particles can include at least one of silver nanoplates, gold nanoparticles, gold nanorods, gold nanocages, multi-walled carbon nanotubes, colloidal magnetite particles, ferrite nanoparticle, or cellulose nanobeads such as blue cellulose nanobeads. Upon exposure to the sample 120, the conjugate material 124 can bind to the analyte 122 therein, thereby forming the analyte-conjugate complex 140 (FIG. 1B).

Referring to FIG. 1B, at a second point in time, the analyte 122 in the sample 120 has bonded to the conjugate material 124 forming the plurality of analyte-conjugate complexes 140. As shown, capillary action moves the plurality of analyte-conjugate complexes 140 across the membrane 112 toward the second end 106. The membrane 112 can include any hydrophilic material, with typical membranes including nitrocellulose, such as nitrocellulose paper. The membrane 112 includes a test line 114 therein. The test line 114 extends from one side of the LFA 101 to the other side of the LFA 101. The test line 114 can be made of a plurality of individual capture molecules 128 (e.g., an antibodies or other molecules capable of retaining the analyte-conjugate complex 140) anchored to the membrane 112 in a line or other suitable configuration, thereby defining the test line 114. The individual capture molecules 128 bind to a portion of individual analyte-conjugate complex 140 thereby retaining the analyte-conjugate complex 140, including the optically-absorbing indicator particles therein. When enough of the plurality of analyte-conjugate complexes 140 are bound to the test line 114, a positive result can be determined. A positive result can be determined visually or more accurately via thermal detection of regions of the assay including optically-absorbing indicator particles 126 collected in large numbers, such as at the test line 114.

Referring to FIG. 1C, at a third point in time, at least some of the plurality of the analyte-conjugate complex 140 have bonded to the plurality of capture molecules 128 and a portion thereof and any unbound conjugate material 124 have passed the test line 114 moving further towards the control line 116. The control line 116 extends from one side of the LFA 101 to the other side of the LFA 101, such as parallel to the test line 114. The control line 116 is made of a plurality of individual control molecules 130 (e.g., antibodies or other molecules capable of retaining one or more of the analyte 122, the conjugate material 124, (including indicator particles), analyte-conjugate complexes 140, or unbound indicator particles) anchored to the membrane 112 in a line or other suitable configuration, thereby collectively defining the control line 116. Typically the individual control molecules 130 bind to a portion of the conjugate material 124. When enough of the plurality of conjugate material 124 is bound to the control line 116, a positive determination that the LFA 101 has functioned properly can be made. A positive determination can be made visually or more accurately via thermal detection of regions containing optically-absorbing indicator particles 126 in the conjugate material 124 collected in large numbers, such as at the control line 116.

FIGS. 2A and 2B are schematic representations of the photothermal spectroscopy (PTS) response of LFAs when the analyte 122 bound to optically-absorbing indicator particles 126 are present and absent therein, respectively. The difference between the PTS response in FIGS. 2A and 2B demonstrates how a positive (FIG. 2A) and negative (FIG. 2B) test result can be viewed via thermal imaging. FIG. 2A depicts LFA 101*a* including a plurality of analyte-conjugate complexes 140 bound to a plurality of capture molecules 128 in a test line 114. Light irradiates at least a portion of the LFA 101*a* at the test line 114 including the plurality of analyte-conjugate complexes 140 at a beam location 230 (e.g., region of the LFA irradiated by the light 231). FIG. 2A also depicts the corresponding temperature profile at the beam location 230.

In contrast to FIG. 2A, FIG. 2B depicts LFA 101*b* in which a plurality of capture molecules 128 form a test line 114. Light irradiates at least a portion of the LFA 101*a*—beam location 230—at the test line 114. FIG. 2B also depicts the corresponding temperature profile at the beam location 230. LFA 101*b* lacks analyte-conjugate complexes 140, which is representative of a negative sample and, therefore, has lower heat capacity than LFA 101*a* due to the lack of optically-absorbing indicator particles 126. The temperature profiles demonstrate that the LFA 101*a* achieves a higher temperature than LFA 101*b*. The temperature profile difference is due to the presence of the optically-absorbing indicator particles in LFA 101*a* and the lack of optically-absorbing indicator particles in LFA 101*b*. The optically-absorbing indicator particles 126 increase the LFAs ability to absorb heat energy, as shown by the photothermal spectrographs.

Figure 3A:
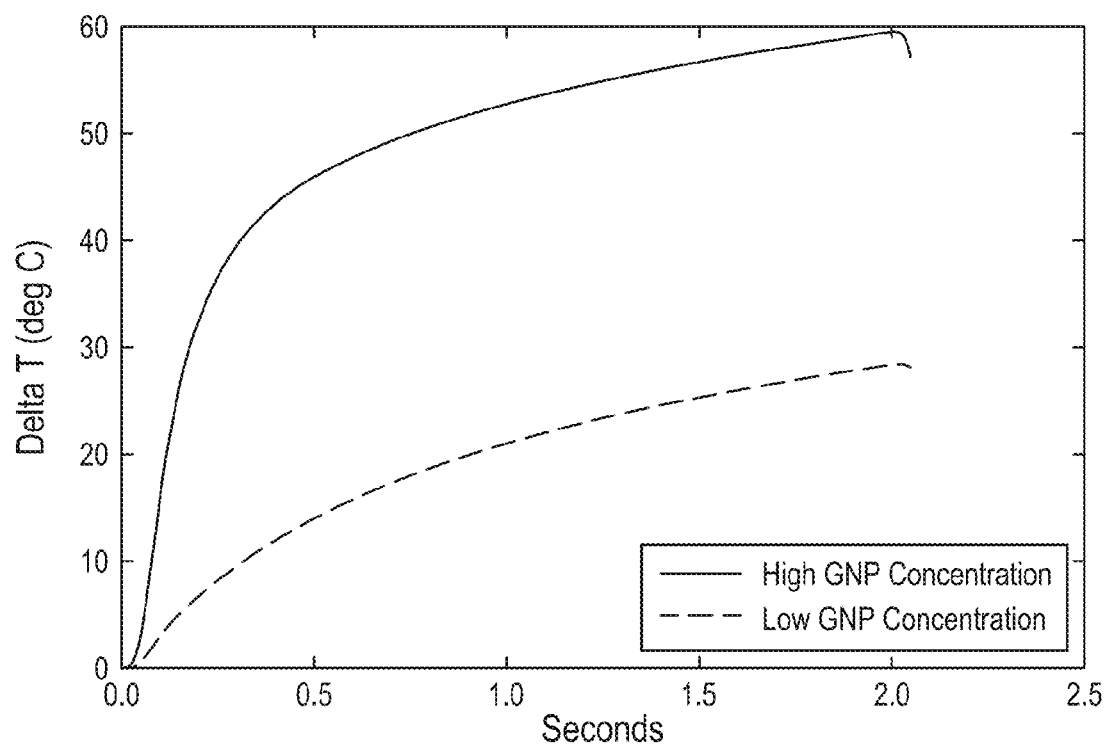
FIG. 3A is a graph of change in temperature versus time for samples having differing gold nanoparticle concentrations.
Figure 3B:
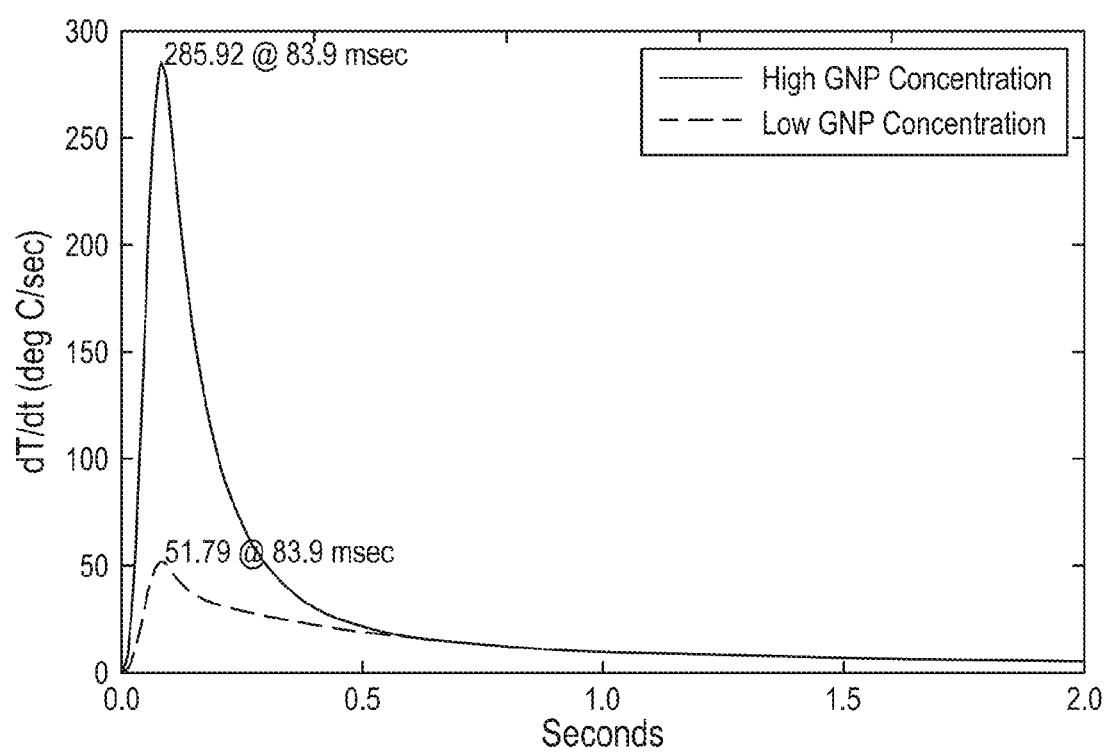
FIG. 3B is a graph of change in temperature per change in time versus time for samples having differing gold nanoparticle concentrations.

The wavelength, intensity, and duration of exposure of light influence how much heat can be stored in an LFA or portions thereof (e.g., optically-absorbing indicator particles). Exposure over longer lengths of time can provide useful information. For example, FIG. 3A is a graph of change in temperature versus time for samples having differing optically-absorbing indicator particle concentrations-high and low respectively. The optically-absorbing indicator particles in this instance were gold nanoparticles. As shown, a higher concentration of gold nanoparticles (GNP) provides a greater change in temperature versus time than a lower concentration of gold nanoparticles. However, the relationship (e.g., proportion) between the high and low concentration change in temperature versus time curves remains relatively constant. FIG. 3B is a graph of change in temperature per change in time versus time for samples having differing optically-absorbing indicator particle concentrations—high and low respectively. The optically-absorbing indicator particles used in the testing for FIG. 3B were also gold nanoparticles. As shown, the change in temperature per change in time versus time curve of the high concentration of gold nanoparticles has a changing proportional relationship to the change in temperature per change in time versus time curve of the low concentration of gold nanoparticles. The graph of FIG. 3B demonstrates that the ratio between the two change in temperature per change in time versus time curves changes over time and eventually converges. However, a ratio between the two curves at near 100 ms shows the point where the largest thermal effect, which correlates with lowest limit of detection, can be achieved. Further samples observed at this point in time within this assay structure can be reliably used to provide the earliest detection due to the largest contrast over background thermal noise. For example, a sample having a lower concentration of analyte-conjugate complex 140 can indicate an emerging or mild case of an illness or condition. Detection of such a low concentration can be contingent upon background thermal noise in an LFA. Determining and testing at the ideal detection time can provide a time at which lower concentrations of an infectious agent, such as a virus, or other analyte can be reliably detected above background noise or temperature characteristics.

A photothermal spectroscopy assay reader can detect the thermal signal or signature of one or more portions of a LFA. Typical photothermal spectroscopy assay readers can include a thermal detector, thermal camera, camera, or an infrared (IR) camera such as an IR camera from FLIR® systems. Photothermal spectroscopy assay readers capable of capturing high frame rate signals (e.g., thermal signals captured at less than about 110 Hz or more than about 9 frames per minute) are expensive and subject to import and export controls. Current U.S. export laws (International Traffic in Arms Regulations (ITAR) and the Export Administration Regulations (EAR)) limit the frame rate at which thermal cameras can legally operate. Thus, to legally observe satisfactory curve accuracy or resolution, a standard photothermal spectroscopy assay reader system cannot be used because the peak of the curve can be cut off or missed due to the necessarily slow frame rate of the ITAR/EAR compliant photothermal spectroscopy assay reader. Embodiments disclosed herein are directed to systems that are both compliant with export control laws and less expensive than a system using a high-frame rate photothermal spectroscopy assay reader.

FIGS. 4A-4E show an embodiment of a system for detecting a presence of an analyte in a LFA. The system 400 includes a support structure 410 having a carriage 420, a light source 430, a photothermal spectroscopy assay reader 440 and a control system 450 secured thereto. During use, the carriage 420 repeatably supports each of a series of LFAs in a work position, wherein the light source 430 can irradiate at least a portion of the LFA (e.g., the test line) in the carriage 420. The work position of the carriage 420 also provides alignment of the field of view of the photothermal spectroscopy assay reader 440 with the irradiated area of the LFA (beam location) so that the photothermal spectroscopy assay reader 440 can capture one or more thermal signals at the beam location. Synchronization of irradiation and thermal imaging can be effectuated by the control system 450. For example, the control system 450 is configured synchronize the capture time of a thermal signal from the photothermal spectroscopy assay reader 440 with the firing time of the light source 430 to provide a series of thermal signals. The control system 450 can be configured to provide time-domain offset synchronization of the capture time of a series of thermal signals from the photothermal spectroscopy assay reader 440 with a series of light emissions of the light source 430 to provide a series of progressively (e.g., sequentially larger) or regressively (e.g., sequentially smaller) time-domain delayed thermal signals.

Figure 4A:
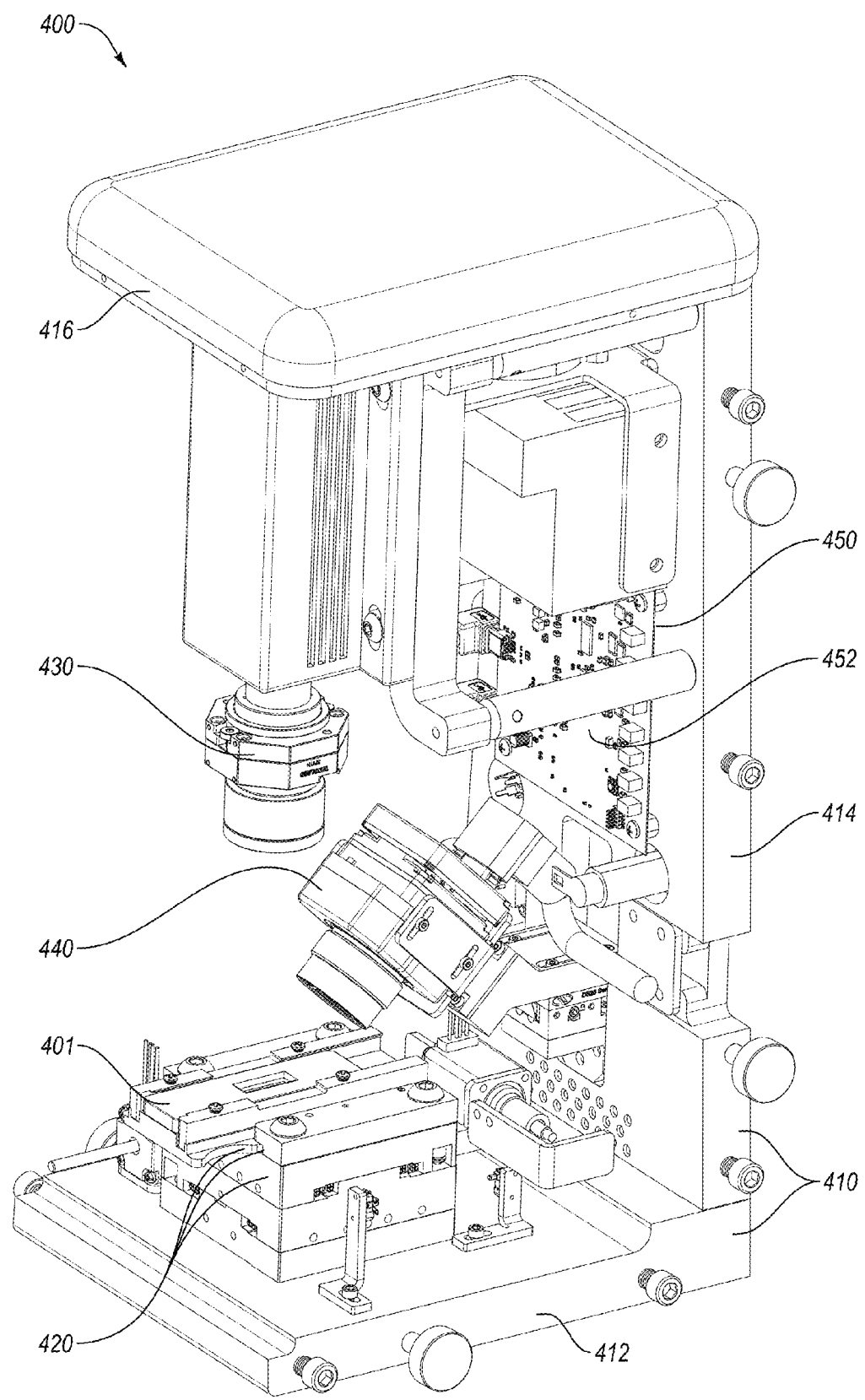
FIG. 4A is an isometric view of a system for detecting a presence of an analyte in an LFA according to an embodiment.
Figure 4B:
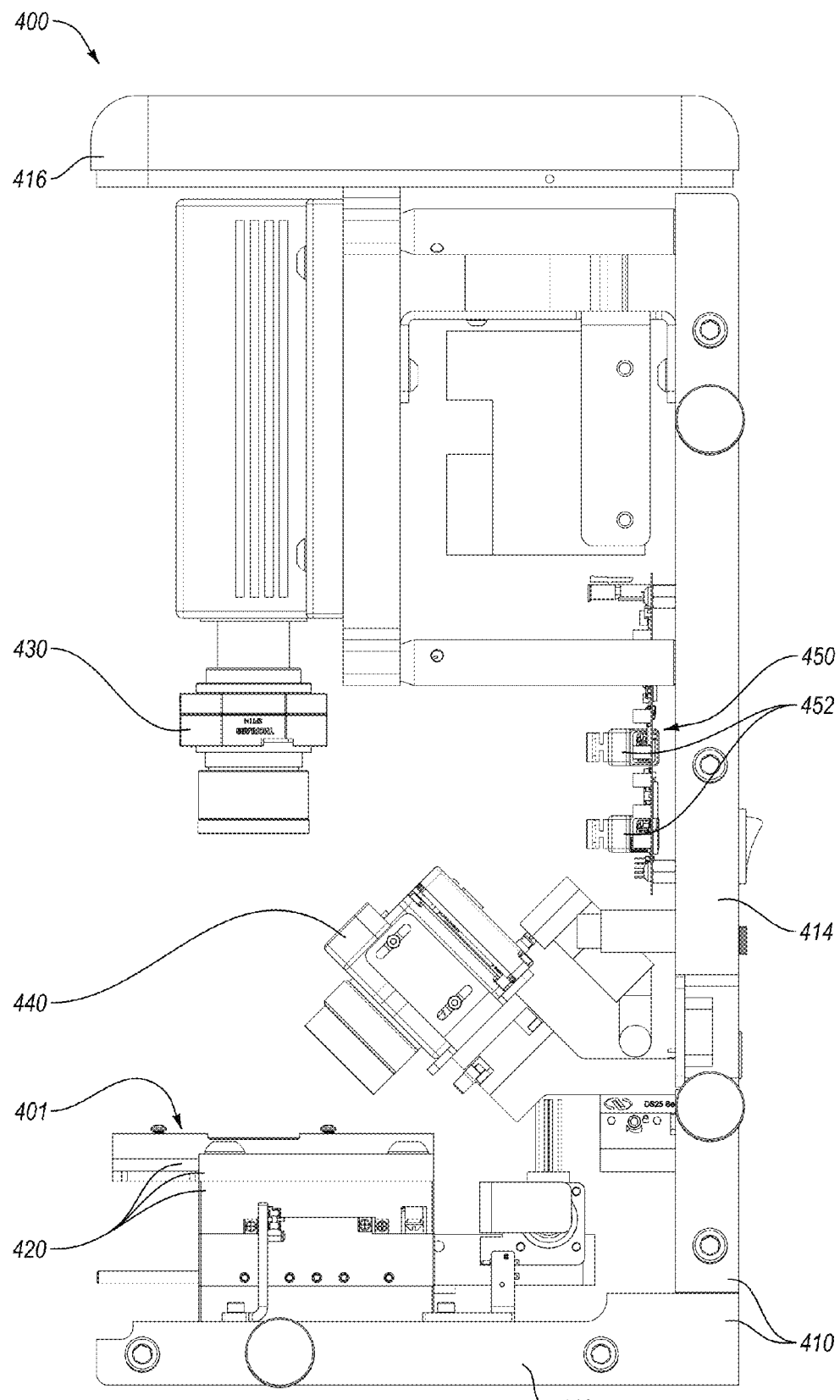
FIG. 4B is a side view of the system of FIG. 4A.

FIG. 4A is an isometric view of the system 400. The support structure can include a base 412; a back support member 414 coupled to the base 412 and extending vertically therefrom; and an upper member 416 coupled to the back support member 414 at a position at or near the top of the back support member 414, the upper member 416 extending horizontally therefrom. One or more portions of the support structure 410 can be made of ceramic, metal (e.g., steel, aluminum, alloys, etc.), plastics, ground stone, or any other material having capable of supporting the components of the system 400 without significantly deforming. FIG. 4B is a side view of the system 400 of FIG. 4A.

The base 412 can support the carriage 420 in a position suitable for sequentially holding any number of LFAs in the work position. The work position aligns a selected portion of the LFA to be irradiated with light from the light source 430 with a field of view of the photothermal spectroscopy assay reader 440 to allow a plurality of thermal signals to be captured by a photothermal spectroscopy assay reader 440.

The carriage can be configured to repeatably retain a series of LFAs in the work position. The carriage 420 can include a tray having a slot therein. For example, the tray can include one or more retention features configured to hold an LFA in the slot. Retention features can include clamps, jaws, adhesives, fasteners, or the like. The slot can be configured to hold a specific type or size of LFA or can be configured to hold many types or sizes of LFAs. The carriage 420 can also include an adjustable work table to which the tray and/or LFAs can be mounted on. The adjustable work table can include any suitable adjustment mechanism suitable to allow movement of the table in one or more directions, such as having slides, ball screws, ways, or other adjustment means extending in one or more of the X, Y, or Z coordinate planes.

The light source 430 can be configured to emit one or more discrete pulses of light, such as a series or plurality of pulses of light. Suitable light sources can include laser light sources or any other high intensity light source capable of delivering focused light and/or heat energy to a target region. For example, the light source 430 can be configured to emit one or more of a plurality of pulses of light responsive to receiving one or more of a plurality of light emission signals, such as light emission signals sent from control electrical circuitry. The light source 430 can be positioned substantially perpendicular to the carriage 420 and/or LFA thereon, such that the light emitted therefrom hits the LFA at about a 90 degree angle. In some embodiments, the light source 430 can be positioned at an angle to the carriage 420 and/or LFA thereon, such that the light emitted therefrom hits the LFA at an incident angle about 45 degrees to about 90 degrees. The light source can be directly or indirectly mounted on or coupled to the back support member 414 or the upper member 416.

The light source 430 can be configured to emit discrete pulses of light of differing durations. For example, the light source 430 can be configured to emit a pulse of light for about 1 ms or more, such as for about 5 ms to about 500 ms, about 50 ms, about 100 ms, about 150 ms, about 200 ms, about 750 ms, about 1 s, or about 2 s. The light source 430 can be configured to emit differing intensities of light including about 50 mW or more, such as about 50 mW to about 1 W, about 101 mW to about 500 mW, about 100 mW to about 200 mW, about 150 mW to about 300 mW, or about 150 mW. The light source 430 can be configured to emit light having one of any differing average wavelengths of light, such as from about 400 nm to about 800 nm. In an embodiment, the light source 430 can be configured to emit green light having an average wavelength between about 495 nm and about 570 nm, such as between about 520 nm and about 550 nm, about 555 nm, or about 535 nm. In an embodiment, the light source 430 can be configured to emit red light having an average wavelength between about 620 nm and about 750 nm, such as between about 630 nm and 680 nm, or about 650 nm. In some embodiments, the system 400 can include two or more light sources 430 which can be configured to emit the same or different characteristics of light (e.g., average wavelength, duration, or intensity of light) from one another. The system 400 can be configured to cause the two or more light sources to emit light substantially simultaneously, in an alternating scheme, or as a backup only on failure of one of the light sources to emit light.

The photothermal spectroscopy assay reader 440 can be configured to capture one or more thermal signals or signatures of at least a portion of the LFA, such as a series of plurality of thermal signals. The photothermal spectroscopy assay reader 440 can be configured to determine the temperature of one or more regions in each thermal signal. Suitable photothermal spectroscopy assay readers 440 can include a thermal camera or an infrared (IR) camera such a FLIR® infrared camera for thermographic imaging from FLIR® Systems, Inc. of Wilsonville, Oreg. The photothermal spectroscopy assay reader 440 can be positioned at an incident angle relative to the upper surface of the LFA on the carriage 430. The photothermal spectroscopy assay reader 440 can be positioned at the incident angle of about 10 degrees or more from the upper surface of the LFA, such as about 10 degrees to about 80 degrees, about 30 degrees to about 60 degrees, or, as shown in FIG. 4B, about 45 degrees. The photothermal spectroscopy assay reader 430 can be directly or indirectly mounted on or coupled to the back support member 414.

The system 400 includes a control system 450 configured to synchronize the time differential between light emission from the light source 420 and thermal signal capture by the photothermal spectroscopy assay reader 440. The control system 450 can be configured to synchronize a progressively or regressively increasing time-domain delay between each light emission from the light source 420 and each corresponding thermal signal capture by the photothermal spectroscopy assay reader 440 for a series of light emissions and corresponding thermal signals. The control system 450 can be configured to synchronize a progressively or regressively offset (e.g., increasing or decreasing) time-domain delay between thermal signal capture by the photothermal spectroscopy assay reader 440 and each corresponding light emission from the light source 420 for a series of light emissions and corresponding thermal signals. The control system can include control electrical circuitry 452. The control system 450 including the control electrical circuitry 452 is operably coupled to one or more of the light source 430 and the photothermal spectroscopy assay reader 440.

One or more components of the control system 450 can be configured to send, receive, coordinate, or process one or more signals to or from one or more of the light source 430 or the photothermal spectroscopy assay reader 440. For example, the control electrical circuitry 452 can be configured to send a plurality of light emission signals to the light source, each light emission signal effective to trigger the light source 430 to emit a pulse of light (e.g., emit a pulse of laser light onto the LFA). The control electrical circuitry 452 can be configured to send a plurality of capture signals to the photothermal spectroscopy assay reader 440, each capture signal effective to cause the photothermal spectroscopy assay reader 440 to capture a thermal signal (e.g., thermal signal of the irradiated portion of the LFA). As discussed in more detail below, the control system 450 can include one or more of a time-delay gate, memory, a user interface, detector control electrical circuitry, a capture trigger, light source control electrical circuitry, an emission trigger, signal relay, or a synchronization signal unit. Any component of the control system 450, such as the control electrical circuitry 452, can be operably coupled to one or more components of the system 400 such as the light source 430, another component of the control system 450, or the photothermal spectroscopy assay reader 440 via a wireless connection or a physical electrical connection (e.g., hard-wiring).

Figure 4C:
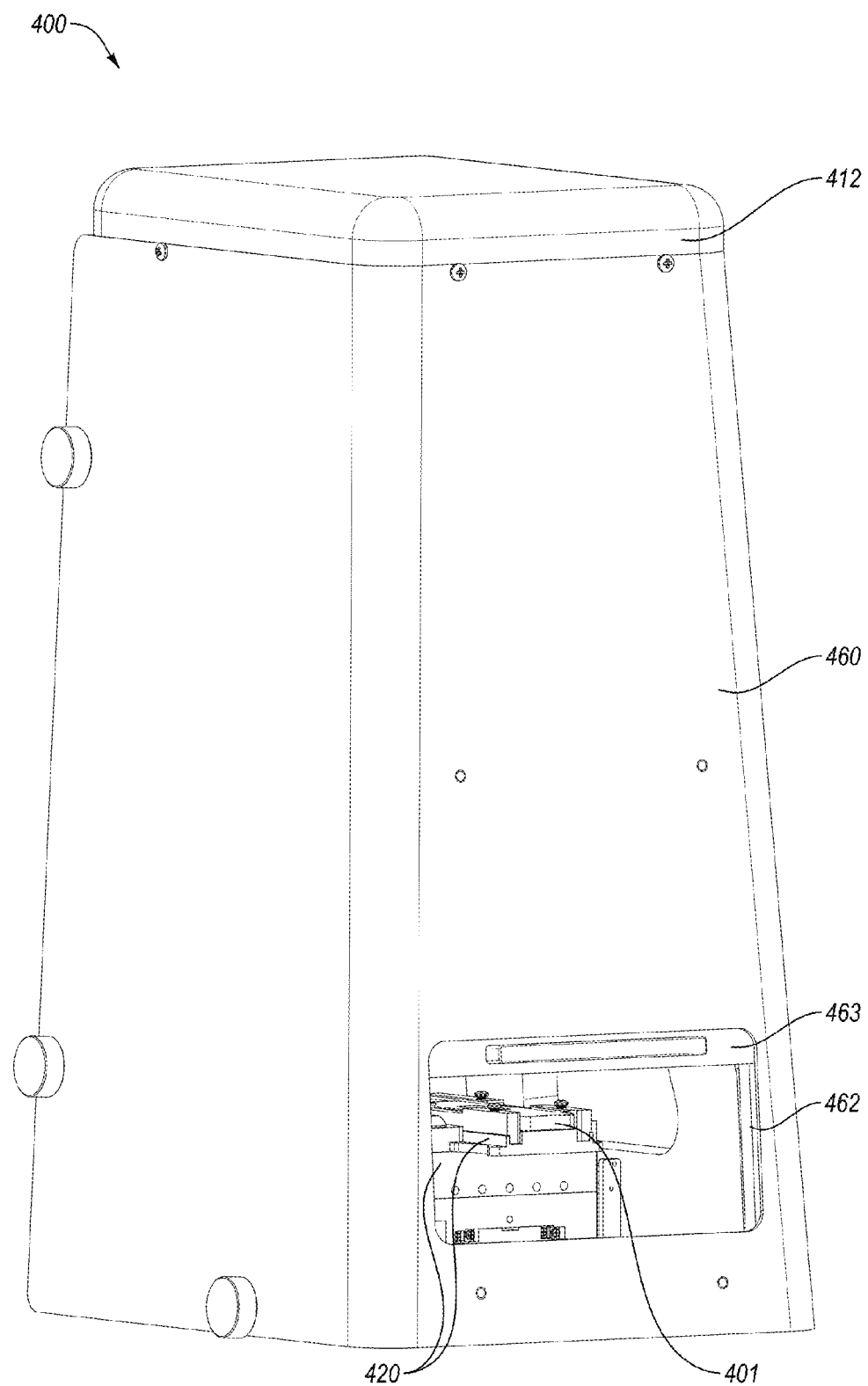
FIG. 4C is an isometric view of the system of FIG. 4A including a cover according to an embodiment.

FIG. 4C shows the system of 400 of FIGS. 4A, 4B, 4D, and 4E with a cover 460 extending about the support structure 410 and enclosing at least a portion of each of the support structure 410, the carriage 420, the light source 430, the photothermal spectroscopy assay reader 440, and the control system 450. The cover 460 can be secured to the support structure 410 at one or more of the base 412, back support member 414, or upper member 416. The cover 460 can be removably secured to the support structure 410 by mechanical fasteners (e.g., posts, screws, bolts, clamps, etc.), adhesives, or magnets. The cover 460 can include one or more of a sheet metal such including aluminum, tin, or steel; plastic (e.g., polycarbonate, delrin, or acrylic); ceramic, or any other suitable material. The cover 460 can include a port 462 configured to allow access to at least a portion of the system 400 during use. The port 462 can be positioned on the front facing portion of the cover and located radially to the carriage 420, such that the carriage 420 including at least the table and slot (if present) are accessible to a user via the port 462. The port 462 can extend laterally from the midpoint of the front face of the cover 460 to points intermediate to the side faces of the cover 460. The port 462 can extend vertically from a lower portion of the front face starting substantially below the carriage 420 and extend to a portion higher up the front face of the cover 460 to a point above the carriage 420 but intermediate to the upper member 416. The port 462 can include a door 463 capable of closing to substantially seal or shield the internal contents of the cover 460 from the external environment. The door 463 can be a sliding door as shown, a hinged door, a rotating door, or any other suitable covering for the port 462.

While depicted as having a substantially vertical arrangement, horizontal or other arrangements of the components of the system 400 are contemplated. For example, a working example (not shown) was constructed having a carriage configured to hold a LFA in a vertical orientation. A laser was positioned laterally horizontal to the LFA and an infrared camera was positioned at an incident angle horizontally lateral to the LFA such that the focal point thereof was aligned with the beam location of the laser thereon.

Figure 4D:
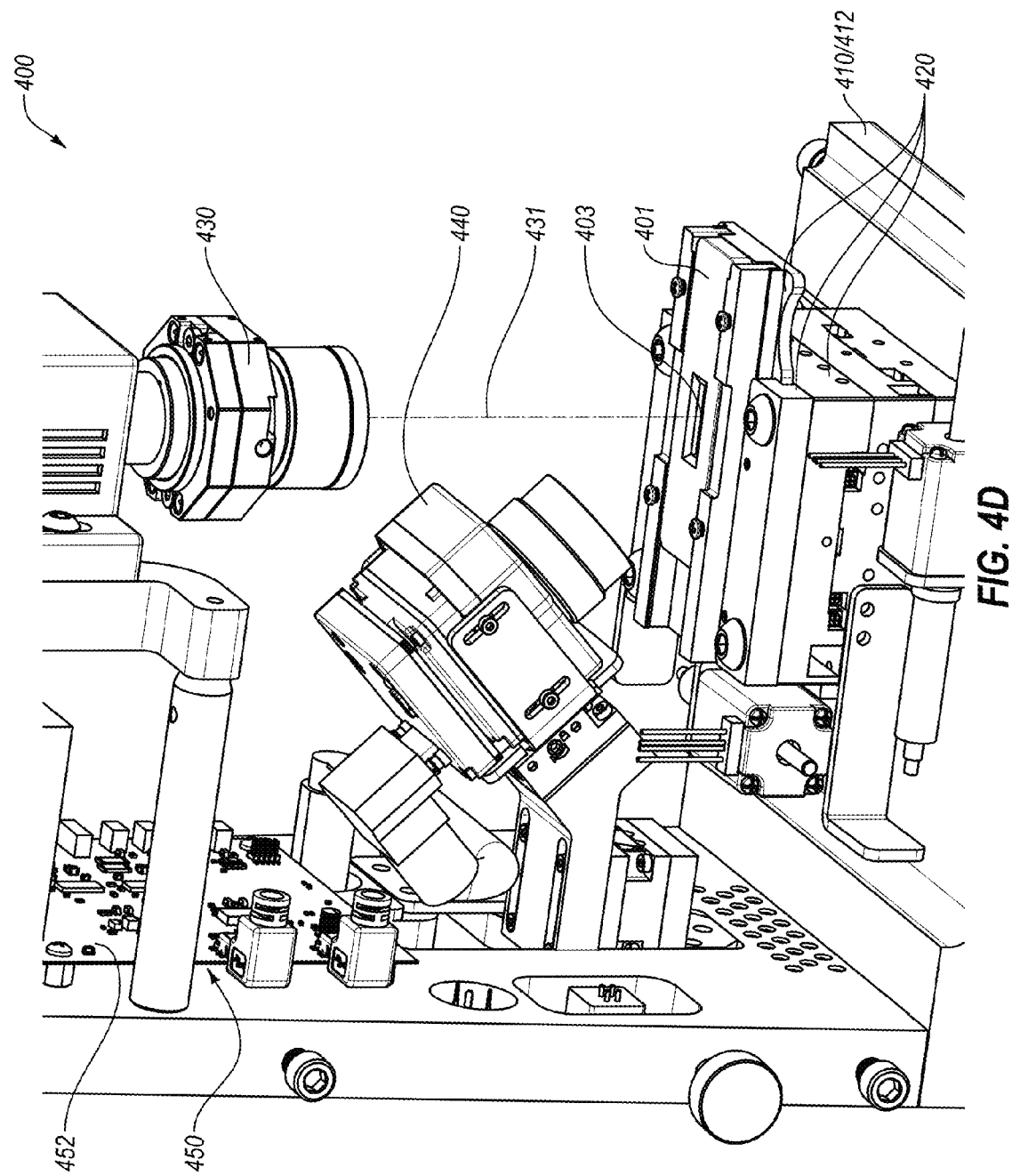
FIG. 4D is an isometric view of part of the system of FIG. 4A during use, according to an embodiment.
Figure 4E:
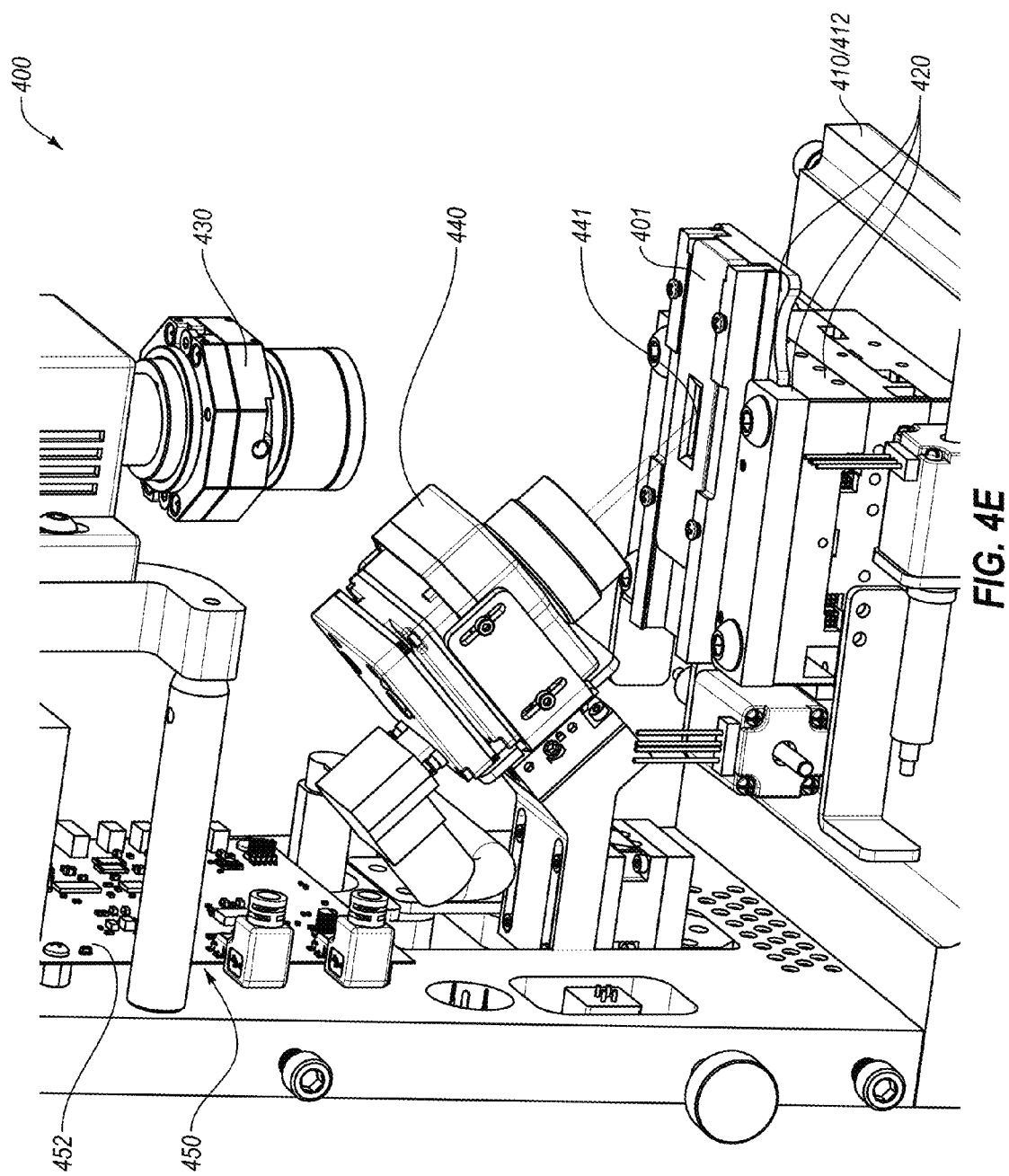
FIG. 4E is an isometric view of part of the system of FIGS. 4A and 4D during use, according to an embodiment.

FIGS. 4D and 4E are isometric views of the system 400 shown in FIGS. 4A and 4B at different times during use. FIG. 4D depicts the system 400 during emission of a pulse of light 431 from the light source 430. The LFA 401 is positioned on the carriage 420 such that the light 431 irradiates a selected portion at the beam location 403 (e.g., the test line irradiated with light) of the LFA 401. The light 431 can induce absorption of radiation resulting in heating of the LFA 401 and any optically-absorbing indicator particles therein.

FIG. 4E depicts the system 400 during capture of a thermal signal of at least the selected portion of the LFA 401. The LFA 401, including the selected portion thereof (e.g., the test line), is positioned in the work position such that the light 431 from the light source 420 irradiates the selected portion at the beam location 403 of the LFA 401 at or near the focal point 441 or field of view of the photothermal spectroscopy assay reader 440. The beam location 403 and the focal point 441 can be substantially coextensive. The photothermal spectroscopy assay reader 440 captures one or more thermal signals at the focal point 441. When the thermal signals are of the irradiated portion of an LFA 401 and the irradiated portion includes the test line of the LFA 401, the presence of an analyte therein can be determined by the thermal signature of the optically-absorbing indicator particles bound thereto. For example, the optically-absorbing indicator particles (e.g., gold nanoparticles) retain more heat than empty capture molecules or underlying membrane material at the test line. Thus, the thermal signal of a positive sample will display in a thermal signal as hotter whereas the thermal signal of a negative sample will display cooler than the positive sample because there are not as many particles capable of retaining the heat applied via the light 431. Additionally, some photothermal spectroscopy assay readers are capable of determining the temperature of different portions of the thermal signal to within an accuracy range of 2 degrees Celsius. In such an embodiment, the photothermal spectroscopy assay reader 440 can take an average temperature reading of one or more portions of one or more thermal signals or an average temperature of the one or more entire thermal signals. The control system 450 can transmit or store such temperature readings correlated to each captured thermal signal for use in analyses as discussed in more detail below.

It should be noted that the system 400 illustrated in FIGS. 4A-4E is merely one of many different embodiments. Other configurations for systems can be used and are contemplated by this disclosure.

Figure 5A:
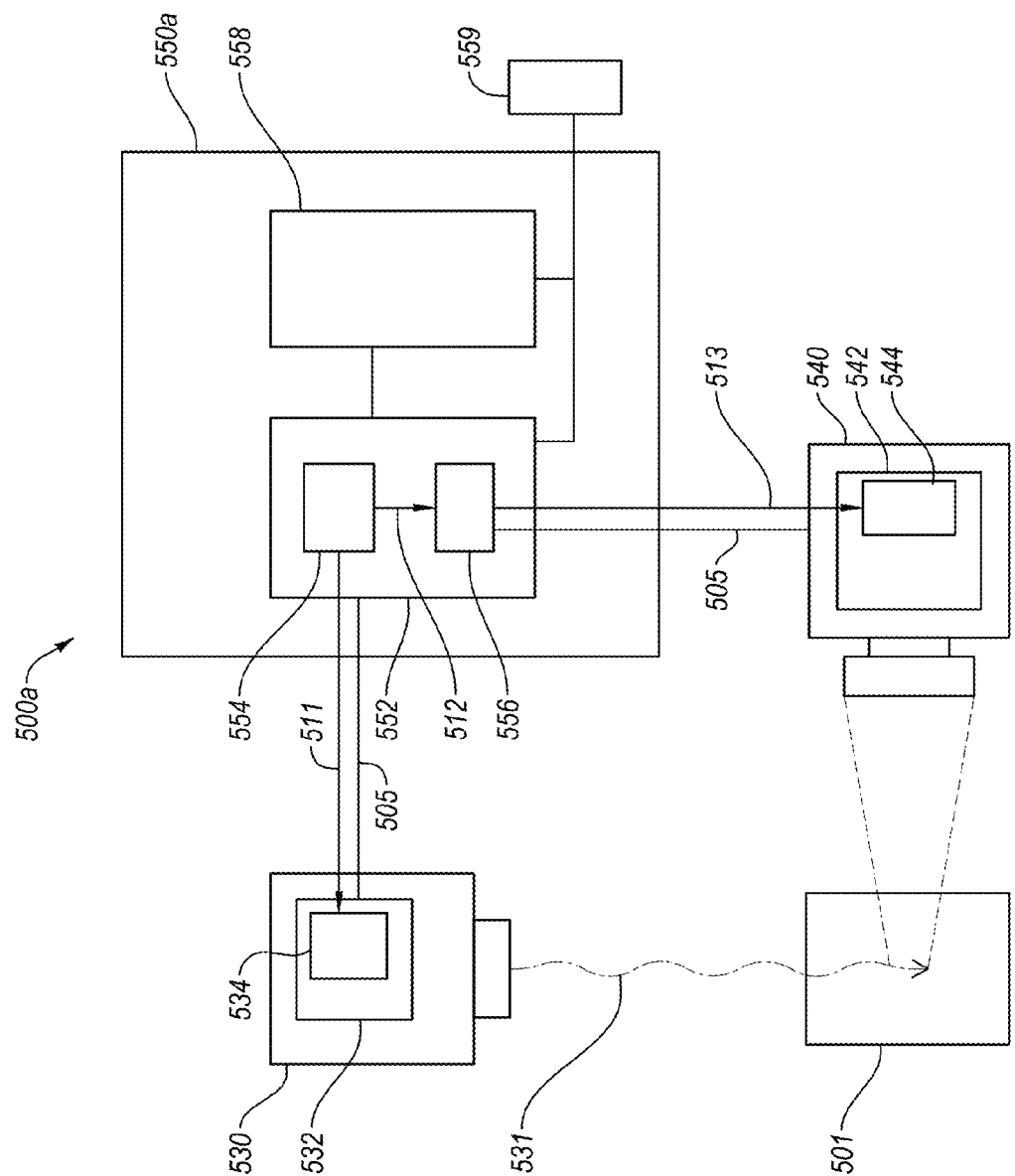
FIG. 5A is a schematic view of a system for detecting a presence of an analyte in a lateral flow assay according to an embodiment.

FIG. 5A is a schematic diagram of an embodiment of a system 500*a* for detecting the presence of an analyte in a sample. The system 500*a* or portions thereof can be identical or similar to the system 400 or portions thereof. The system 500*a* can include a light source 530, a photothermal spectroscopy assay reader 540, and a control system 550*a*. The control system 550*a* can be operably connected to one or both the light source 530 or the photothermal spectroscopy assay reader 540 via one or more connections 505. The connections 505 can be wireless or physical electrical connections (e.g., wires or circuits).

In an embodiment, the system 500*a* is a light source or control electrical circuitry paced system in which each light emission or signal directing the same initiates capture of a corresponding thermal signal or signal directing the same.

The control system 550*a* includes control electrical circuitry 552, which can be directly or indirectly coupled to one or more of the light source 530 or the photothermal spectroscopy assay reader 540 via one or more connections 505. The control electrical circuitry 552 can include one or more of a signal relay 554 or a time-delay gate 556 each of which is also configured as any of the suitable electrical circuitry disclosed herein. The control electrical circuitry 552 can be configured to direct the signal relay 554 to send one or more of a plurality of light emission signals 511 to the light source 530 and one or more of a plurality of capture signals 512 to the photothermal spectroscopy assay reader. In an embodiment, the control electrical circuitry 552 is configured to synchronize sending a series of light emission signals 511 with a series of capture signals 512, with each light emission signal 511 being synchronized with a corresponding capture signal 512. In an embodiment, the control electrical circuitry 552 is configured to synchronize sending each subsequent capture signal 512 with a progressively or regressively offset time-domain interval or delay from each corresponding light emission signal 511 in the series of light emission signals. For example, the control electrical circuitry 552 can be configured to offset capturing each thermal signal in a series of time-delayed thermal signals by a fixed time-domain delay (e.g., about 5 milliseconds (ms) or about 10 ms) in multiples thereof (e.g., the fixed time-domain delay, followed by two times the fixed time-domain delay, follows by three times the fixed time-domain delay, etc.). For example, a capture signal 512 can be sent from the signal relay 554 at the same time that the light emission signal 511 is sent from the signal relay 554, the immediately subsequent capture signal 512 can be sent a fixed time-domain delay later than the light emission signal 511 is sent to the light source 530, and the following subsequent capture signal 512 can be sent two fixed time-domain delays later than the corresponding light emission signal is sent to the light source 530, and so on. Similarly, the offset between signals can be regressively offset by the fixed time-domain delay (e.g., 30 ms, then 25 ms, then 20 ms, then 15 ms, etc.). Suitable fixed time-domain delays can be selected based upon one or more of the suspected analyte type, the capture molecules, the optically-absorbing indicator particles used, the light source, or the photothermal spectroscopy assay reader. A suitable fixed time-domain delay can be 1 second or less, such as about 500 ms or less, about 100 ms or less, about 50 ms or less, about 30 ms or less, about 20 ms or less, about 10 ms or less, about 9 ms or less, about 7 ms or less, about 5 ms, or less, about 3 ms or less, or about 1 ms. A suitable fixed time-domain can be 3 ms or more, such as about 5 ms to about 20 ms, about 5 ms or more, about 7 ms or more, about 10 ms or more, about 15 ms or more, about 20 ms or more, or about 30 ms or more.

In an embodiment, the control electrical circuitry 552 includes a time-delay gate 556 configured to receive, optionally offset or delay, and then relay one or more signals. The time-delay gate 556 can be configured to progressively or regressively delay sending each subsequent signal in a series of signals by the fixed time-domain delay. The time-delay gate 556 can be operably coupled to and between the signal relay 554 and the photothermal spectroscopy assay reader 540. For example, the time-delay gate 556 can be configured to receive a series of capture signals 512 (each sent from the signal relay substantially simultaneously with each of a series of light emission signals) from the signal relay 554 and progressively offset or delay sending each subsequent time-delayed capture signal 513 in a series of time-delayed capture signals by a progressively increasing multiple of the fixed time-domain delay (e.g., 5 ms, then 10 ms, then 15 ms, etc.).

The control electrical circuitry 552 or one or more components thereof, such as the time-delay gate 556 or signal relay 554, can include a timer or counter (e.g., one or more monostable circuits) configured to delay signal transmission therethrough for a set time period. The time-domain intervals or time-domain delays can be programmed or hardwired into the control electrical circuitry 552, such as by having one or more monostable circuits therein. Suitable programming can be effectuated at a user interface as detailed below.

In response to receiving each light emission signal 511 of the series of light emission signals, the light source 530 emits a pulse of light 531 onto the selected portion of the LFA 501 including onto any optically-absorbing indicator particles therein. Responsive to receiving each time-delayed capture signal 513 of the now progressively time-delayed series of capture signals, the photothermal spectroscopy assay reader captures a time-delayed thermal signal of the selected portion of the LFA 501 including any optically-absorbing indicator particles therein. In an embodiment, a fixed time-domain delay can be 10 milliseconds or more and a series of thermal signals can be obtained whereby the capture time of each thermal signal, as related to the corresponding light emission, is offset 10 milliseconds or more later than the previous thermal signal. In an embodiment, a series of temperatures of the irradiated region can be obtained or determined whereby the thermal signal showing the temperature, as related to the corresponding light emission, is offset 10 milliseconds or more later than the previous thermal signal. In some embodiments, the temperature of the portion of the flow assay irradiated with light in each thermal signal of a series of thermal signals can be determined, such as by examining each thermal signal with a computer program, or determined directly from the photothermal spectroscopy assay reader. A graph of change in temperature versus time (FIG. 3A) or change in temperature per change in time versus time (FIG. 3B) can be constructed and analyzed using the temperature data from the series of progressively or regressively time-delayed thermal signals.

The control system 550a or one or more components thereof can be operably coupled to the light source 530 and the photothermal spectroscopy assay reader 540. In an embodiment, the control electrical circuitry 552 is operably coupled to the light source 530 and the and the photothermal spectroscopy assay reader 540.

In an embodiment, the light source 530 is configured to emit one or more pulses of light responsive to receiving the light emission signal 511 from the control electrical circuitry 552 or a component thereof (e.g., the signal relay). The control system 550a or the light source 530 can include light source control electrical circuitry 532 configured to control the light source 530, such as controlling, regulating, sending, or receiving signals and data therefrom or therein (e.g., controlling or initiating emission of light including one or more of the intensity, duration, beam width, or average wavelength thereof). Such control can be responsive to receiving one or more signals (e.g., one of a plurality of light emission signals). In an embodiment, the light source control electrical circuitry 532 can be disposed in the light source 530 (as shown in FIG. 5A), in this sense the light source 530 can also be said to include the light source control electrical circuitry 532. In an embodiment (not shown), the light source control electrical circuitry 532 can be disposed at a position outside of the light source 530 such as in an associated control box or in the control electrical circuitry 532. As shown, the light source control electrical circuitry 532 can include an emission trigger 534 configured to control (e.g., initiate) emission of one or more pulses of light responsive to receiving a light emission signal 511 from the control electrical circuitry 552 or a component thereof (e.g., the signal relay). The emission trigger 534 can be operably coupled to the control electrical circuitry 552 and the light source 530, such as via the light source control electrical circuitry 532 to communicate therewith (e.g., send or receive signals).

In an embodiment, the photothermal spectroscopy assay reader 540 is configured to capture one or more thermal signals responsive to receiving a capture signal 512 or 513 from the control electrical circuitry 552 or a component thereof (e.g., the signal relay or time-delay gate). The control system 550a or the photothermal spectroscopy assay reader 540 can include detector control electrical circuitry 542 configured to control the photothermal spectroscopy assay reader 540, such as controlling, sending, and receiving signals and data therefrom or therein (e.g., controlling or initiating thermal signal capture or thermal signal data). For example, the detector control electrical circuitry 542 can be configured to control the repeating fixed time-domain interval between each successive thermal signal of the plurality of thermal signals. The fixed time-domain interval is the fixed space in time between similar actions, such as between capture of thermal signals. In an embodiment, the detector control electrical circuitry 542 can be disposed in the photothermal spectroscopy assay reader 540 (as shown in FIG. 5A), in this sense the photothermal spectroscopy assay reader 540 can also be said to include the detector control electrical circuitry 542. In an embodiment (not shown), the detector control electrical circuitry 542 can be disposed at a position outside of the photothermal spectroscopy assay reader such as in an associated control box or in the control electrical circuitry 542. As shown, the detector control electrical circuitry 542 can include a capture trigger 544 configured to control (e.g., initiate) capture of one or more thermal signals responsive to receiving a capture signal 512 or 513 from the control electrical circuitry 552 or a component thereof. For example, the capture trigger 544 can also be configured as any of the suitable electrical circuitry disclosed herein. The capture trigger 544 can be operably coupled to the control electrical circuitry 552 and the photothermal spectroscopy assay reader 540, such as via the detector control electrical circuitry 542 to communicate therewith (e.g., send or receive signals). The detector control electrical circuitry 542 can be configured to send each thermal signal of a plurality of thermal signals to the control electrical circuitry 552 or memory unit 558.

In an embodiment, during operation, the control electrical circuitry 552 or a component thereof, such as the signal relay 554 can send a series of light emission signals to the light source 530 or a component thereof (e.g., light source control electrical circuitry 532 or emission trigger 534) at fixed or equally spaced time-domain intervals. The control electrical circuitry 552 or a component thereof, such as the signal relay 554 or time-delay gate 556 can send a series capture signals to the photothermal spectroscopy assay reader 540 or a component thereof (e.g., detector control electrical circuitry 542 or capture trigger 544) at progressively or regressively offset time-domain intervals or delays as spaced from the corresponding light emission signals.

In an embodiment, the control electrical circuitry 552 or a component thereof can be configured to send a series of light emission signals to the light source 530 and a series of capture signals to the detector control electrical circuitry 542. Each light emission signal having a corresponding and substantially simultaneously sent capture signal therewith. Each subsequent capture signal of the series of capture signals can include a progressively larger or smaller time-domain delay therewith, effective to cause the detector control electrical circuitry 542 or capture trigger to offset capturing a thermal signal by the space of time indicated by the time-domain delay, such that the corresponding thermal signal is captured at a progressively greater or smaller time-delay than an immediately previous thermal signal.

In an embodiment, the control system 550*a* can include a memory unit 558 configured to store thermal signals, light emission characteristics, operational programs, or other data thereon. The memory unit 558 can include a non-transitory memory device such as a hard drive, a solid state memory device, or any other suitable electronic medium capable of allowing storage and retrieval of data thereon. The memory unit 558 can include one or more sample types or related operational programs stored thereon. Operational programs can include computer instructions to carry out a specific set of process parameters upon execution of the operational program. Operational parameters include timing programs including one or more of fixed time-domain intervals between light emission signals, the progressive or regressive time-domain delay such as between subsequent capture signals corresponding to each of the light emission signals; one or more of the intensity, duration, or wavelength of light emitted from the light source 530; relationships of the suspected analyte or a sample type to the any of the preceding parameters such as in a look-up table; or combinations thereof.

In an embodiment, during operation, the suspected analyte can be correlated in a look-up table with a set of operational parameters that can be selected either manually or automatically based upon a particular suspected analyte (e.g., based upon inputting the particular suspected analyte into the control system 550*a*). In an embodiment, the control electrical circuitry 552 is configured to determine or select a timing program including one or more of the desired fixed time-domain interval, time-domain delay, or offset time-domain interval or delay. The control electrical circuitry 552 can select the timing program responsive to the sample type selected by a user, such as by comparing the sample type with time information corresponding thereto in a look-up table stored in the memory unit 558. In an embodiment, the control electrical circuitry 552 can include a comparative analysis circuit configured to correlate the selected sample type with one or more timing programs in the memory and execute the correlated one or more timing programs responsive thereto.

In an embodiment, during operation, a LFA type or structure can be correlated in a look-up table with a set of operational parameters that can be selected either manually or automatically based upon a particular assay (e.g., based upon inputting the particular assay model number into the control system 550*a*). In an embodiment, the control electrical circuitry 552 is configured to determine or select a timing program including one or more of the desired fixed time-domain interval, time-domain delay, or offset time-domain interval or delay. The control electrical circuitry 552 can select the timing program responsive to the assay type selected by a user, such as by comparing the assay type with time information corresponding thereto in a look-up table stored in the memory unit 558. In an embodiment, the control electrical circuitry 552 can include a comparative analysis circuit configured to correlate the selected assay type with one or more timing programs in the memory and execute the correlated one or more timing programs responsive thereto.

The control system 550*a* can include a user interface 559 operably coupled thereto. The user interface 559 can be operably coupled to the control electrical circuitry 552 or the memory unit 558. The user interface 559 can be secured to the system 500*a*, integrated into the support structure 510, wirelessly connected to one or more components of the system 500*a*, or otherwise operably coupled thereto. In an embodiment, the user interface 559 includes a screen configured to display one or more thermal signals, graphs based on the thermal signals, or positive/negative results of testing for an analyte. In an embodiment, the user interface 559 can include one or more of a keypad, a screen, a personal computing device (e.g., a laptop or desktop computer, a tablet computer, a cellular phone, etc.), a switch, a selector, or a power controller. In an embodiment, during use, a user can input, instructions, data, or operational programs (e.g., timing or light characteristic programs) into the control system 550*a* via the user interface 559 wherein the data is sent to the memory unit 558 or the control electrical circuitry. In an embodiment, the user interface 559 can be used to output or retrieve stored information such as thermal signal data from the memory 558. Responsive to user input, such as a suspected analyte type, the control electrical circuitry 558 can correlate the suspected analyte type with a corresponding operational program having operational parameters (e.g., time-domain delay, light emission intensity, light emission duration, number of corresponding light emission-thermal signal pairs, etc.) selected to provide satisfactory analysis of the particular suspected analyte type. In an embodiment, responsive to user input, the system 500*a* can initiate operation. In an embodiment, responsive to user input, the system 500*a* can set or adjust one or more operational parameters.

In an embodiment, the control electrical circuitry 552 can be configured to analyze each of the thermal signals or temperature data corresponding thereto and build a graph based on a series of time-delayed thermal signals, temperature, and timing data therein; the graph having a curve (e.g., a change in temperature per change in time versus time curve) comprising data points representing each time-delayed thermal signal in a series of time-delayed thermal signals. In an embodiment, the control electrical circuitry 552 can be configured to analyze the curve and determine the ideal detection time (e.g., time at which the maximum value for change in temperature per change in time occurs) for a suspected analyte, such as by identifying the peak of the change in temperature per change in time versus time curve. In an embodiment, the control electrical circuitry 552 can be configured to analyze the curve and determine the ideal detection time (e.g., time at which the maximum value for change in temperature per change in time occurs) for a specific structure, type or model of LFA, such as by identifying the peak of the change in temperature per change in time versus time curve. The control electrical circuitry 552 can output the data corresponding to the time-delayed thermal signals (e.g., graph, ideal detection time, or positive/negative results of the test) to one or both of the user interface 559 or the memory unit 558. In an embodiment, responsive to determining the ideal detection time, the control electrical circuitry 558 can automatically set a fixed test delay time to the ideal detection time so that any number of subsequent test samples are only tested at the ideal detection time to provide greater sensitivity and confidence in results of each test.

The system 500a can also include a power supply (not shown) operably coupled to one or more components of the system 500a. The power supply can be operably coupled to the system 500a or any component thereof either directly or indirectly. The power supply can include a power cable configured to mate with a power outlet (e.g., wall mount power outlet), or one or more batteries.

Figure 5B:
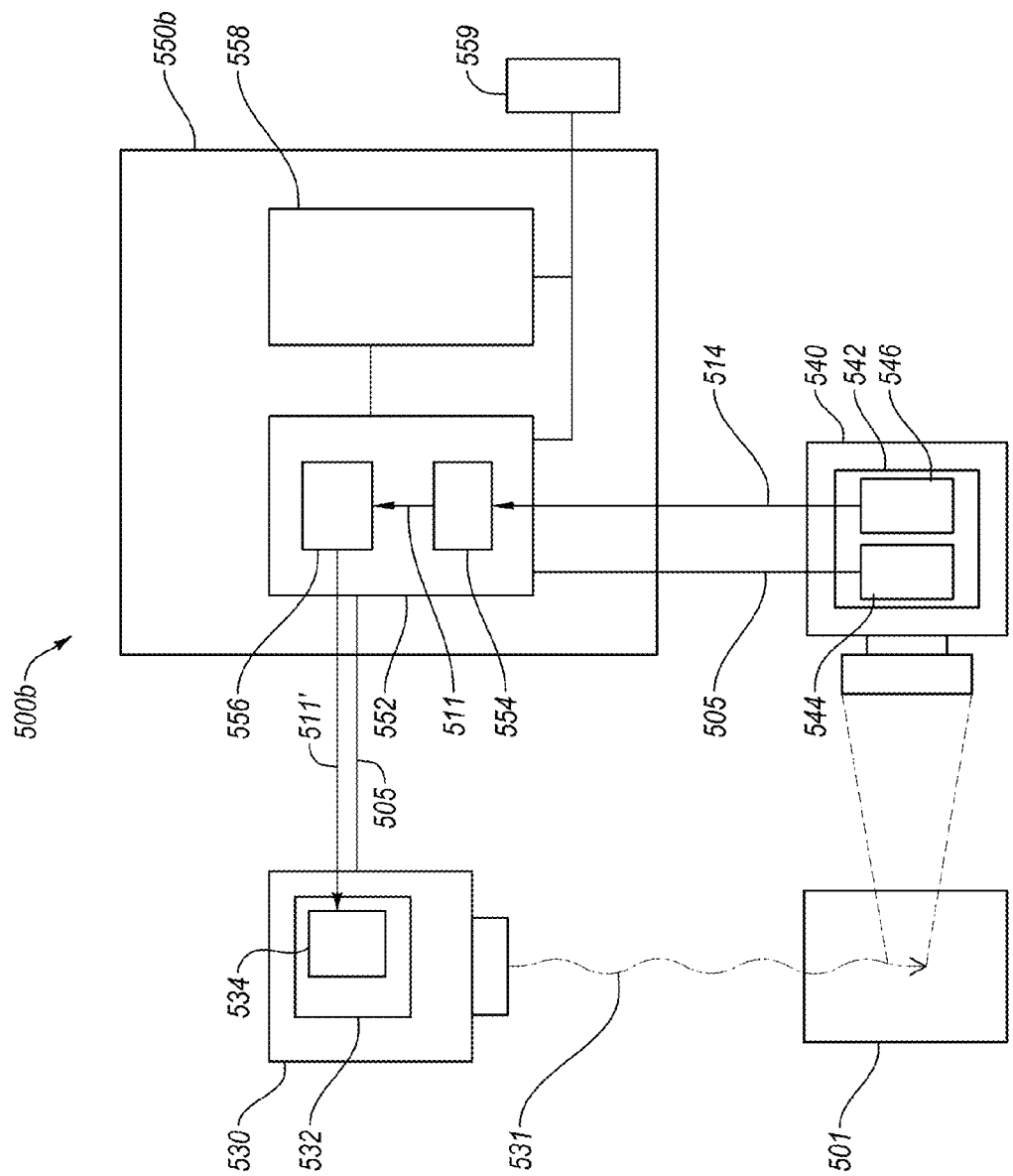
FIG. 5B is a schematic view of a system for detecting a presence of an analyte in a lateral flow assay according to an embodiment.

FIG. 5B is a schematic diagram of a system 500b for detecting the presence of an analyte in a sample. The system 500b can include a light source 530, a photothermal spectroscopy assay reader 540, and a control system 550b. The control system 550b can be operably connected to one or both the light source 530 or the photothermal spectroscopy assay reader 540 via one or more connections 505. The connections 505 can be wireless or physical electrical connections (e.g., wires or circuits). Components of the system 500b having reference numerals corresponding to identically numbered components of system 500a can be similar or identical thereto including all components therein. For example, the light source 530 of the system 500b is identical or similar to the light source 530 described above, including the associated light source control electrical circuitry 532 or emission trigger 534.

In an embodiment, the system 500b is a photothermal spectroscopy assay reader 540 paced system in which each capture of a thermal signal initiates a related light emission.

The control system 550b includes control electrical circuitry 552, which can be directly or indirectly coupled to one or more of the light source 530 or the photothermal spectroscopy assay reader 540 via one or more connections 505. The control system 500b can further include a memory unit 558 and a user interface 559 substantially as described above. The control electrical circuitry 552 can include or be operably connected to one or more of a signal relay 554, a time-delay gate 556, the memory unit 558, or the user interface 559. The control electrical circuitry 552 can be configured to direct the signal relay 554 to send one or more of a plurality of light emission signals 511 to the light source 530, send one or more of a plurality of capture signals 512 to the photothermal spectroscopy assay reader 540, and receive one or more synchronization signals 514.

In an embodiment, the photothermal spectroscopy assay reader 540 is configured to capture one or more thermal signals responsive to receiving a capture signal from the control electrical circuitry 552 or a component thereof (e.g., the signal relay). The control system 550b or the photothermal spectroscopy assay reader 540 can include detector control electrical circuitry 542 configured to control the photothermal spectroscopy assay reader 540, such as controlling, sending, and receiving signals and data therefrom or therein (e.g., controlling or initiating thermal signal capture or thermal signal data, or controlling synchronization signals corresponding to the capture of a thermal signal). In an embodiment, the detector control electrical circuitry 542 can be disposed in the photothermal spectroscopy assay reader 540 (as shown in FIG. 5B), in this sense the photothermal spectroscopy assay reader 540 can also be said to include the detector control electrical circuitry 542. In an embodiment (not shown), the detector control electrical circuitry 542 can be disposed at a position outside of the photothermal spectroscopy assay reader such as in an associated control box or in the control electrical circuitry 542. As shown, the detector control electrical circuitry 542 can include a capture trigger 544 configured to control (e.g., initiate) capture of one or more thermal signals responsive to receiving a capture signal from the control electrical circuitry 552 or a component thereof. The capture trigger 544 can be operably coupled to the control electrical circuitry 552 and the photothermal spectroscopy assay reader 540, such as via the detector control electrical circuitry 542. The control electrical circuitry 552 or the capture trigger 544 can be configured to direct the capture of a series of thermal signals at evenly spaced fixed time-domain intervals of every 100 ms or more, such as every 110 ms to every 500 ms, every 120 ms to every 200 ms, every 110 ms, every 150 ms, every 110 ms or more, every 120 ms or more, every 150 ms or more, every 200 ms or more, every 500 ms or more, or every 1 second or more.

The control system 550b or the photothermal spectroscopy reader 540 can include a synchronization signal unit 546 operably coupled thereto, such as in a portion of the detector control electrical circuitry 542. For example, the synchronization signal unit 546 can also be configured as any of the suitable electrical circuitry disclosed herein. The synchronization signal unit 546 can be operably coupled to one or more of the control electrical circuitry 552, the photothermal spectroscopy assay reader 540, the detector control electrical circuitry 542, or the capture trigger 544, either directly or indirectly such as via the detector control electrical circuitry 542. The synchronization signal unit 546 is configured to send one or more of a plurality of synchronization signals 514, such as in a series, to the control electrical circuitry 552 or to a component therein. Each synchronization signal 514 indicates occurrence or time of the capture of a thermal signal. The detector control electrical circuitry 542 or the capture trigger 544 can be programmed to execute or receive capture signals spaced by a fixed time-domain offset effective to trigger the capture of a plurality of thermal signals at evenly spaced intervals. Upon capturing each thermal signal, the synchronization signal unit 546 is configured to substantially simultaneously send a synchronization signal 514 reporting the thermal signal capture to the control electrical circuitry 552.

In an embodiment, and as discussed in more detail below, the control electrical circuitry 552 is configured to synchronize sending a series of light emission signals 511 to the light source 530 responsive to each of a series of synchronization signals 514, with each light emission signal 511 being synchronized with a corresponding synchronization signal 514. In an embodiment, the control electrical circuitry 552 is configured to synchronize sending each subsequent time-delayed light emission signal 511' with a progressively or regressively offset time-domain delay from each corresponding synchronization signal 514 in the series of synchronization signals. For example, the control electrical circuitry 552 can be configured to offset sending each light emission signal in a series of light emission signals by a progressively or regressively offset time-domain delay (e.g., about 5 mms or about 10 milliseconds) in multiples thereof. In an embodiment, the control electrical circuitry 552 can include the time-delay gate 556 operably coupled to the signal relay and the light source 530 or a component thereof. The time-delay gate 556 can be configured to offset sending each light emission signal of a series of light emission signals by a progressively offset time-domain delay from the each corresponding successive synchronization signal.

The control electrical circuitry 552 can be configured to receive each of the plurality of synchronization signals from the synchronization signal unit 546 and responsive thereto, relay a corresponding light emission signal 511 for each of the synchronization signals 514 to the light source 530. In an embodiment, the control electrical circuitry 552 can include a signal relay 554 configured to receive or send one or more signals therefrom. The signal relay 554 can be configured to receive each of the plurality of synchronization signals 514 from the synchronization signal unit 546 and responsive thereto, relay a corresponding light emission signal 511 for each of the synchronization signals 514 to the light source 530.

In an embodiment, the control system 550b can include a time-delay gate 556. The time-delay gate 556 can be operably coupled to and between the control electrical circuitry 552 and the light source 530. For example, the time-delay gate 556 can be positioned between and coupled to the signal relay 556 and the light source control electrical circuitry 532 or the emission trigger 534 therein. In an embodiment, the time-delay gate 556 is configured to receive a series of light emission signals 511 from the control electrical circuitry 552 (e.g., signal relay) and relay a series of progressively or regressively time-delayed light emission signals 511', each after a selected time-domain delay has elapsed. For example, the time-delay gate 556 can be configured to receive the light emission signal 511 from the signal relay 556 and delay sending a corresponding time-delayed light emission signal 511' by a fixed time-domain delay, such as 10 ms or more, and upon receiving the subsequent light emission signal 511, delay the corresponding time-delayed light emission signal 511' by a subsequent multiple of the fixed time-domain delay such as by 20 ms, and so on. The time-delay gate can be directed by or receive program instructions from the control electrical circuitry 552, directing or programming the selected fixed time-domain delay therein. Suitable fixed time-domain delays can be selected based upon one or more of the analyte, the capture molecules, the optically-absorbing indicator particles used, the light source, or the photothermal spectroscopy assay reader. A suitable fixed time-domain delay can be 1 ms or more, such as about 3 ms to about 20 ms, about 5 ms or more, about 7 ms or more, about 9 ms or more, about 10 ms or more, about 15 ms or more, about 20 ms or more, or about 30 ms or more.

In an embodiment, the light source 530 is configured identically or similar to the light source 530 described above with respect to system 500a. The control system 550b or the light source 530 can include light source control electrical circuitry 532 configured identically or similar to the light source control electrical circuitry 532 described above with respect to system 500a. As shown, the light source control electrical circuitry 532 can include an emission trigger 534 configured identically or similar to the emission trigger 534 described above with respect to system 500a.

Responsive to receiving each time-delayed light emission signal 511' of the now progressively time-delayed series of light emission signals, the light source 530 irradiates the selected portion of the LFA 501 with light. Subsequently, the photothermal spectroscopy assay reader 540 captures a time-delayed thermal signal of the selected portion of the LFA 501 including any optically-absorbing indicator particles therein. In an embodiment, the fixed time-domain delay can be 10 milliseconds or more and a series of thermal signals can be obtained whereby the capture time of each thermal signal, as related to the corresponding light emission, is offset 10 milliseconds later than the previous thermal signal. In an embodiment, a series of temperatures of the irradiated region can be obtained whereby the observed temperature as related to the corresponding light emission is offset 10 milliseconds later than the observed temperature in the previous measurement. A graph of change in temperature versus time (FIG. 3A) or change in temperature per change in time versus time (FIG. 3B) can be constructed and analyzed using the temperature data from the series of progressively or regressively time-delayed thermal signals.

In an embodiment, the control system 550b can include a memory unit 558 which can be similar or identical to the memory unit 558 described with respect to the system 300a. The memory unit 558 can include one or more operational programs stored thereon, which can additionally include the fixed time-domain interval for the photothermal spectroscopy assay reader or the fixed time-domain delay for the control electrical circuitry.

The control system 550b can include a user interface 559 operably coupled thereto. The user interface 559 can be identical or similar to the user interface 559 described with respect to system 500a. In an embodiment, responsive to user input, the system 500b can initiate operation. In an embodiment, responsive to user input, the system 500b can set or adjust one or more operational parameters.

In an embodiment, the control electrical circuitry 552 can be configured to analyze each of the thermal signals or temperature data corresponding thereto; build a graph based on a series of time-delayed thermal signals, temperature, and timing data therein; analyze the constructed graph; or output results or data related thereto identically or similarly as described above.

The system 500b can also include a power supply (not shown) operably coupled to one or more components of the system 500b. The power supply can be operably coupled to the system 500b or any component thereof either directly or indirectly. The power supply can include a power cable configured to mate with a power outlet (e.g., wall mount power outlet), or one or more batteries.

Figure 6:
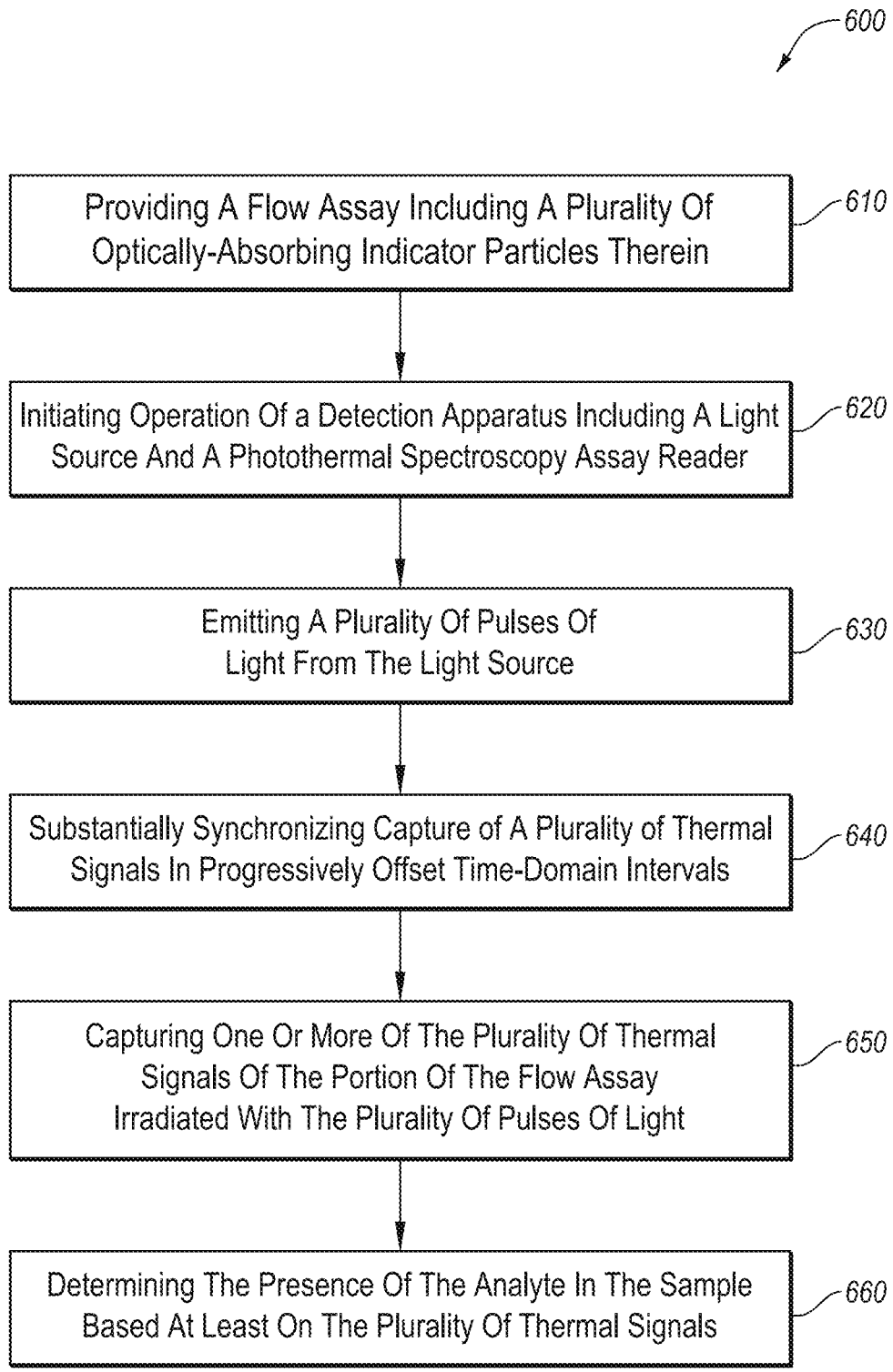
FIG. 6 is a flow chart of a method of detecting a presence of an analyte in a sample according to an embodiment.

FIG. 6 is a flow diagram of an embodiment of a method 600 for detecting a presence of an analyte in a sample. The method 600 includes capturing time-domain delayed thermal signals of a portion of an LFA (including any optically-absorbing indicator particles therein) that has been irradiated with light by a series of light emissions to determine an ideal time to determine the most sensitive and accurate time of detection (as related to the time of irradiation) of an analyte in a sample, and then determining if an analyte is in the sample based on the data gleaned from the thermal signals. The method 600 includes an act 610 of providing or securing a flow assay including a plurality of optically-absorbing indicator particles therein to a carriage of a detection apparatus. In an embodiment, detection apparatus can be any of the systems described herein. In an embodiment, the flow assay can be similar to identical to any flow assay described herein, including an LFA. Securing the flow assay to the carriage can include inserting the flow assay into a slot on the carriage, such as to position the flow assay in the work position. Securing the flow assay to the carriage can include one or more of tightening a clamp, tightening jaws, using adhesives, tightening fasteners, or adjusting the position of the table of the carriage.

The method 600 includes an act 620 of initiating operation of a detection apparatus including a light source and a photothermal spectroscopy assay reader configured to capture a plurality of thermal signals of the flow assay including the plurality of optically-absorbing indicator particles therein. In an embodiment, initiating operation of the detection apparatus can include turning the detection apparatus (e.g., system 400, 500a, or 500b) on, pressing a start button, or providing user instructions to start the detection apparatus (e.g., providing a start command at the user interface). In an embodiment, the detection apparatus is configured to initiate automatically responsive to detecting a LFA in the work position. In an embodiment, the light source can be similar or identical to any light source described herein and the photothermal spectroscopy assay reader can be similar or identical to any photothermal spectroscopy assay reader disclosed herein.

The method 600 includes an act 630 of emitting a plurality of pulses of light from the light source onto at least a portion of the flow assay. In an embodiment, emitting a plurality of pulses of light onto at least a portion of the flow assay includes emitting a plurality of pulses of light onto the flow assay at or near the test line. In an embodiment, emitting a plurality of pulses of light onto at least a portion of the flow assay includes emitting a series of pulses of light onto the flow assay. In an embodiment, emitting a plurality of pulses of light onto at least a portion of the flow assay includes emitting a series of time-delayed pulses (as related to a thermal signal capture time or synchronization signal) of light onto the flow assay. In an embodiment, emitting a plurality of pulses of light onto at least a portion of the flow assay includes emitting a plurality of pulses of laser light from a laser light source, such as laser light having an average wavelength in the green or red visible light region. Emitting a plurality of pulses of light from the light source onto at least a portion of the flow assay can include emitting one or more of any of the wavelengths of light, durations of pulsed light, intensities of light, or beam widths of light disclosed therein.

The method 600 includes an act 640 of substantially synchronizing capture of a plurality of thermal signals in progressively offset time-domain intervals or delays, the plurality of thermal signals being of the at least a portion of the flow assay irradiated with the plurality of pulses of light. In an embodiment, substantially synchronizing capture of a plurality of thermal signals in progressively offset time-domain intervals includes sending a plurality of light emission signals from the control electrical circuitry to the light source, each of the plurality of light emission signals effective to trigger at least one pulse of light from the light source responsive thereto. In an embodiment, substantially synchronizing capture of a plurality of thermal signals in progressively offset time-domain intervals includes sending a plurality of capture signals from the control electrical circuitry to the photothermal spectroscopy assay reader at a progressively offset time-domain delay between each successive light emission signal of the plurality of light emission signals and sending (e.g., relaying) a capture signal corresponding thereto. Each of the plurality of capture signals is effective to cause the photothermal spectroscopy assay reader to measure the temperature of or capture a thermal signal of the portion of the flow assay responsive thereto.

In an embodiment, substantially synchronizing capture of a plurality of thermal signals in progressively offset time-domain intervals or delays, the plurality of thermal signals of the at least a portion of the flow assay irradiated with the plurality of pulses of light can include sending a plurality of synchronization signals from the photothermal spectroscopy assay reader to the control electrical circuitry. Each of the plurality of synchronization signals indicating capture time of a corresponding thermal signal. Substantially synchronizing capture of a plurality of thermal signals in progressively offset time-domain intervals can include, responsive to the each of the plurality of synchronization signals, sending one or more light emission signals from the control electrical circuitry to the light source. Each of the plurality of light emission signals can be sent at a progressively offset time-domain interval from the corresponding synchronization signal and is effective to trigger emission of a light pulse from the light source.

Techniques and systems for substantially synchronizing capture of a plurality of thermal signals in progressively offset time-domain intervals or delays are further described herein with respect to FIGS. 4A-5B, 7A and 7B.

The method 600 includes an act 650 of capturing one or more of the plurality of thermal signals of the at least a portion of the flow assay irradiated with the plurality of pulses of light. In an embodiment, capturing one or more of the plurality of thermal signals of the at least a portion of the flow assay irradiated with the plurality of pulses of light is responsive to receiving a series of capture signals, each capture signal effective to cause capture of a corresponding thermal signal. In an embodiment, capturing one or more of the plurality of thermal signals of the at least a portion of the flow assay irradiated with the plurality of pulses of light includes sending a synchronization signal 514 reporting the thermal signal capture to the control electrical circuitry 552.

In an embodiment, capturing one or more of the plurality of thermal signals of the at least a portion of the flow assay irradiated with the plurality of pulses of light includes capturing a series of thermal signals at a progressively larger offset time-domain interval or delay from each successive pulse of light of a series of pulses of light. For example, the offset time-domain interval can be increased by at least 1 ms upon each successive emission of light of a plurality of pulses of light, such as by about 3 ms, 5 ms, 10 ms, 15 ms, 20 ms, or about 30 ms.

In an embodiment, capturing one or more of the plurality of thermal signals of the at least a portion of the flow assay irradiated with the plurality of pulses of light includes capturing a series of thermal signals at a progressively smaller (e.g., regressive) offset time-domain interval from each successive pulse of light of a series of pulses of light. For example, the offset time-domain interval can be reduced by at least 1 ms upon each successive emission of light of a plurality of pulses of light, such as by about 3 ms, 5 ms, 10 ms, 15 ms, 20 ms, or about 30 ms.

The act of capturing one or more of a plurality of thermal signals can include any of the details about capturing thermal signals described herein.

The method 600 includes an act 660 of determining the presence of the analyte in the sample based at least partially on the plurality of thermal signals. For example, determining the presence of the analyte can include examining one or more thermal signals of a sample and comparing the temperature information from the one or more thermal signals with a determined detection limit (e.g., noise level) to determine if the thermal information from the one or more thermal signals is above the detection limit. In an embodiment, a user can determine the presence of an analyte in a sample by taking a series of time-domain delayed thermal signals of a sample irradiated with light as described herein and constructing a change in temperature versus change in time curve or a change in temperature per change in time versus time curve. Subsequently and as explained in more detail below with respect to FIGS. 8A and 8B, a user or a computing device can determine from the curve the ideal detection time or the noise limit. A user can test the sample or additional samples at the ideal detection time to yield the highest sensitivity or accuracy of results. For example if a test sampled at the determined ideal detection time exhibits a temperature, change in temperature, or change in temperature per change in time over the determined detection limit, then the sample can be confidently noted as positive. The absorption of radiation from the light source by the optically-absorbing indicator particles, as shown in the thermal signals, demonstrates a temperature above that determined to be noise or background heat. If the test data is below the noise limit, then the sample can be confidently noted as negative.

In an embodiment, determining the presence of the analyte in the sample based at least partially on the plurality of thermal signals can include building a curve based on a series of offset time-domain thermal signals, and comparing the sample curve to a standard or known curve to determine if there is a correspondence indicative of a positive result therebetween. For example, the shape of the curves (e.g., indicative of change in temperature versus time or change in temperature per change in time versus time) can differ between a positive sample having more optically-absorbing indicator particles therein and a negative sample having no or background amounts of optically-absorbing indicator particles therein.

FIG. 7A is a graphical representation of the progressively increasing time-domain delay between signals from a system for detecting the presence of an analyte in a sample according to an embodiment. Referring to FIG. 7A and the system 500a in FIG. 5A, in an embodiment, the light emission signal 511a can be sent from control electrical circuitry 552 to the light source 530 to trigger an emission of light 531 therefrom. A corresponding capture signal 512a can be substantially simultaneously sent from the control electrical circuitry 552 to the photothermal spectroscopy assay reader 540 to trigger capture of a thermal signal. A subsequent light emission signal 511b is sent from the control electrical circuitry 552 after a fixed time-domain interval (e.g., 100 ms) has elapsed with a corresponding capture signal 512b sent thereafter by an additional a time-domain delay. The time-domain delay can be any time-domain delay disclosed herein, such as 10 ms or more. The resulting thermal signal is captured 10 ms after the corresponding light emission or 110 ms after the initial thermal signal is captured. Subsequently, a third light emission signal 511c can be sent after another fixed time-domain interval has passed (e.g., another 100 ms) with a corresponding capture signal 512c being sent thereafter by a subsequent multiple of the time-domain delay, such as 20 ms (e.g., two times the 10 ms time-domain delay). The resulting thermal signal is captured 20 ms after the corresponding light emission or 110 ms after the second thermal signal is captured. Another iteration of the above technique can be carried out with the time-domain delay between light emission signal 511d and capture signal 512d being 30 ms again spaced from the previous thermal signal capture by 110 ms. In this way, a progressively offset time-domain interval or delay can be observed between each light emission and corresponding thermal signal in a series of thermal signals as shown by the observed offset.

In an embodiment (not shown), the initial light emission signal 511a can be sent from control electrical circuitry 552 to the light source 530 to trigger an emission of light 531 therefrom. A corresponding capture signal 512a can be substantially simultaneously sent from the control electrical circuitry 552 to the photothermal spectroscopy assay reader 540 to trigger capture of a thermal signal. A subsequent light emission signal 511b is sent from the control electrical circuitry 552 after a fixed time-domain interval (e.g., 250 ms) has elapsed with a corresponding capture signal 512b being sent spaced thereafter by an additional period of the fixed time-domain interval less than a time-domain delay. The time-domain delay can be any time-domain delay disclosed herein, such as 25 ms. The resulting thermal signal is captured 225 ms after the first light emission signal 511a or 25 ms before the second light emission signal 511b. Subsequently, a third light emission signal 511c can be sent after another fixed time-domain interval has passed (e.g., another 250 ms) with a corresponding capture signal 512c being spaced from the second light emission signal 511b by the fixed time-domain interval less a subsequent multiple of the time-domain delay, such as 50 ms (e.g., two times the 25 ms time-domain delay). The resulting thermal signal is captured 200 ms after the light emission 511b or 50 ms before the light emission signal 511c. Another iteration of the above technique can be carried out with the spacing between the light emission signal 511c and capture signal 512d being 175 ms. The spacing between capture signals remains 225 ms while the spacing between the light emission and thermal signal capture time iteratively decreases. In this way, a regressively offset time-domain interval or delay can be observed between each light emission and corresponding thermal signal in a series of thermal signals.

FIG. 7B is a graphical representation of the progressively offset time-domain interval or delay between signals from a system for detecting the presence of an analyte in a sample within a flow assay according to an embodiment. Referring to FIG. 7B and the system 500b in FIG. 5B, in an embodiment, the synchronization signal 514a from a series of synchronization signals can be sent to the control electrical circuitry 552, and a second synchronization signal 514b is sent to the control electrical circuitry 552, whereby the control electrical circuitry 552 can determine the fixed time-domain interval therebetween or send a light emission signal 511a. For the purposes of this disclosure, use of the term light emission signal 511 can include time-delayed light emission signal 511' as context dictates. Each synchronization signal 514a-d corresponds to capture of a thermal signal by the photothermal spectroscopy assay reader. Responsive to the determined fixed time-domain interval, the control electrical circuitry can send a light emission signal 511a to the light source 530, which can occur substantially simultaneously with the receipt of the second synchronization signal 514b to thereby demonstrate a first observed offset equal to the fixed time-domain interval. Subsequent light emission signals can be progressively or regressively offset by a fixed time-domain delay from the next synchronization signal as predicted or determined by the control electrical circuitry 552 using the determined fixed time-domain interval. For example, the control electrical circuitry 552 is configured to offset sending the next corresponding light emission signal 511b by a progressively or regressively offset time-domain delay such as 10 ms, such that the observed time delay or observed offset between the light emission 531 triggered by the light emission signal 511b and the captured thermal signal noted by the subsequent synchronization signal 514c is about 10 ms. Upon additional iterations of the same technique, the observed time delay between synchronization signal 511c and next corresponding capture signal 514d is about 20 ms, and so on.

Put another way, the offset time-domain delay between a synchronization signal (e.g., 514a) and corresponding emission signal (e.g., 511a) is greater than the offset time-domain delay between the subsequent synchronization signal (e.g., 514b) and corresponding emission signal (e.g., 511b) by the next multiple of the fixed time-domain delay, while the observed offset between the light emission signal (e.g., 511a-c) and subsequent synchronization signal (e.g., 514b-d) increases by the same amount. By this technique a series of time-delayed thermal signals can be captured, the series of thermal signals capturing a progressively increasing observed offset or time delay between light emissions and the corresponding thermal signals in the series of thermal signals.

In an embodiment (not shown), a series of synchronization signals reporting corresponding thermal signal captures is sent from the synchronization signal unit 546 at 110 ms intervals. The synchronization signals 514a-514d from a series of synchronization signals can be sent to the control electrical circuitry 552 with a fixed time-domain interval between each synchronization signal (e.g., equidistantly spaced by 110 ms). Responsive to the synchronization signal 514a, the control electrical circuitry 552 can send a light emission signal 511a to the light source 530 after a time-domain delay equal to the fixed time-domain interval of 110 ms so that the light emission 511 coincides with the next predicted synchronization signal 514b. Responsive to receipt of the immediately subsequent synchronization signal 514b, the control electrical circuitry is configured to offset the corresponding light emission signal 511b by a fixed time-domain delay (e.g., 10 ms) plus the fixed time-domain interval of 110 ms (e.g., 10 ms after the next predicted synchronization signal 514c). Responsive to receipt of the immediately subsequent synchronization signal 514c, the control electrical circuitry is configured to offset the corresponding light emission signal 511 by a multiple of the fixed time-domain delay (e.g., multiple of 2 resulting in 20 ms) plus the fixed time-domain interval of 110 ms (e.g., 20 ms after the next predicted synchronization signal 514c) from the next predicted synchronization signal 514d. More iterations of the acts above can be carried out until a satisfactory observed offset or time delay between thermal signals is observed. By this technique a series of time-delayed thermal signals can be captured, the series of thermal signals capturing a progressively decreasing observed offset or time-domain delay between light emissions and the corresponding thermal signals in the series of thermal signals.

In an embodiment, sending a plurality of capture signals 512 from the control electrical circuitry 552 to the photothermal spectroscopy assay reader 540 at a progressively offset time-delay between each subsequent light emission signal 511 and corresponding capture signal 512 can include sending each capture signal 512 at an offset time-domain delay of at least about 110 ms.

In an embodiment, the system 400, 500a, or 500b can be configured to operate in one or more of the manners described herein (e.g., control progressively or regressively offset time-domain delays, paced by the control electrical circuitry as in FIG. 5A or paced by the photothermal spectroscopy assay reader as in FIG. 5B). In any of the embodiments herein, the photothermal spectroscopy assay reader can determine the temperature of a portion of the flow assay directly or can capture a series of thermal signals of the portion of the flow assay and the control system can include an executable program configured to determine the temperature in each of the series of thermal signals.

Any of the techniques described herein be carried out for as many iterations as desired or needed, such as to build a graph having a curve of change in temperature per change in time versus time using each discrete point in time as a point on the curve. For example, a user can use 5 or more iterations, such as 10 iterations, 20 iterations, or 30 iterations. The fixed time-domain interval can be 100 ms or more, such as about 110 ms or more, about 150 ms, about 200 ms, about 250 ms, about 300 ms, about 500 ms, about 1 s, or about 1 or more minutes. While smaller fixed time-domain intervals are contemplated herein, time-domain intervals having spacing of about 110 ms or more are particularly useful for the purposes of this application. The time-domain delay or fixed time-domain delay can be about 1 ms or more, such as about 3 ms, about 5 ms, about 10 ms, about 15 ms, about 25 ms, about 50 ms, about 100 ms, about 1 second or more, or about 1 minute or more.

While the time-domain intervals between subsequent thermal signals remain constant (e.g., 110 ms) in the above embodiments, some embodiments can include progressively increasing or decreasing time-domain intervals between subsequent thermal signals in a series of thermal signals. For example, the time-domain delay between thermal signals in a series of thermal signals can progressively increase by 5 ms or more upon each subsequent thermal signal in the series of thermal signals, such as 110 ms, then 115 ms, followed by 120 ms, etc. Time-domain intervals can be progressively offset by 5 ms or more, such as about 5 ms to about 1 s, about 10 ms to about 500 ms, about 20 ms to about 100 ms, about 5 ms, about 10 ms, or about 20 ms.

While the time-domain intervals, delays, and offset time-domain intervals herein have been described as progressively offset, in some embodiments, the time-domain intervals or time-domain delay intervals can be randomly offset so long as the relationship between light source emission and subsequent thermal signal capture is known or recorded. For example, a series of randomly time-domain offset thermal signals (e.g., thermal signals having randomly spaced offset time-domain delays between the light source emission and thermal signal capture) can be directed and captured, and subsequently the thermal signals can be placed in order of the offset time-domain delay of each thermal signal, such as by a user or automatically by the control system of the systems described herein. A graph can be built of the change in temperature per change in time versus time, or change in temperature versus time using each discrete point in time as a point on the curve.

Figure 8A:
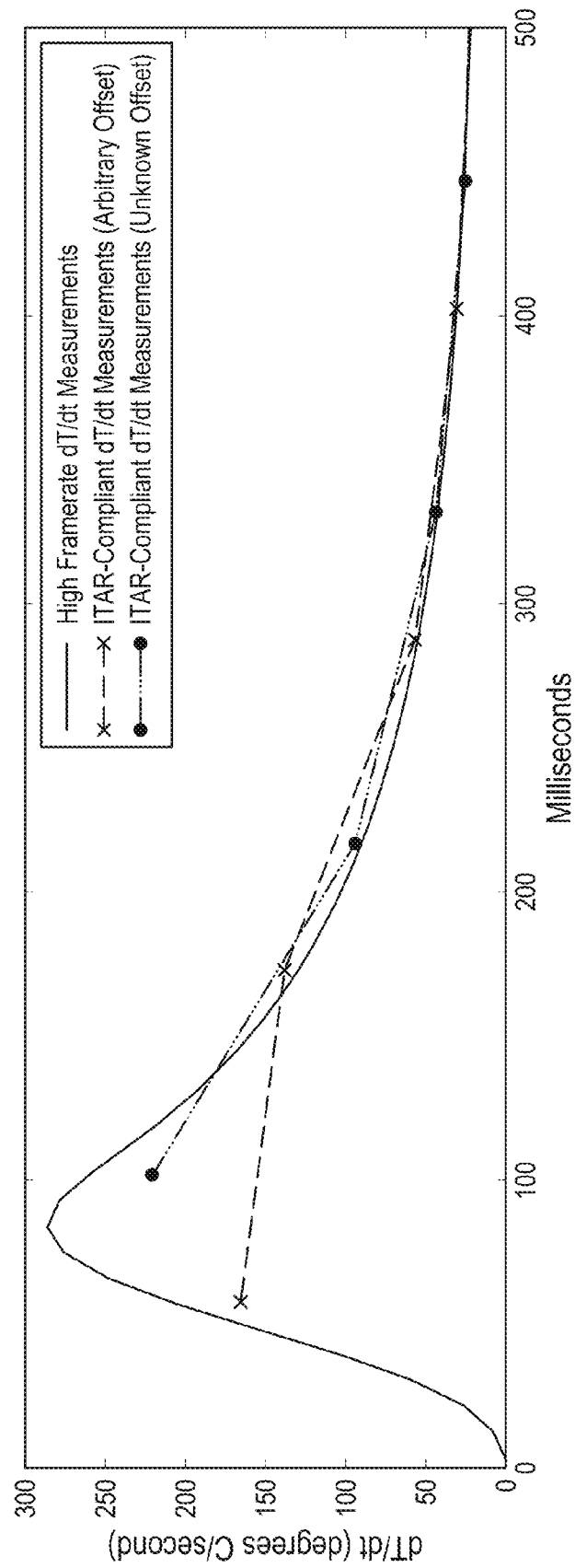
FIG. 8A is a graph of change in temperature per change in time versus time curve with comparative curves constructed with measurement points spaced by an arbitrary amount.

FIG. 8A is a graph of a change in temperature per change in time versus time curve with comparative curves constructed with measurement points spaced by an arbitrary amount. The graph shows a high frame rate change in temperature per change in time curve based upon measurements taken at intervals well under 110 ms. The graph shows a constructed curve based upon change in temperature per change in time measurements taken at times spaced by an arbitrary offset of about 100 ms. The graph shows a constructed curve based upon change in temperature per change in time measurements taken at times spaced by an arbitrary offset of about 100 ms but at different points along the time axis. As shown, both of the constructed curves miss the true ideal detection time point at the peak of the high frame rate curve. Further, as time progresses all of the curves converge to background or noise levels in a similar manner as the high and low nanoparticle concentration curves shown in FIG. 3B, above which accurate detection may not be possible. For this reason, a sufficient amount of iterations of the techniques disclosed herein, showing sufficiently close time-domain offsets therebetween, allow for construction of a graph showing or at least closely approximating the peak of change in temperature per change in time versus time (e.g., ideal detection time).

Figure 8B:
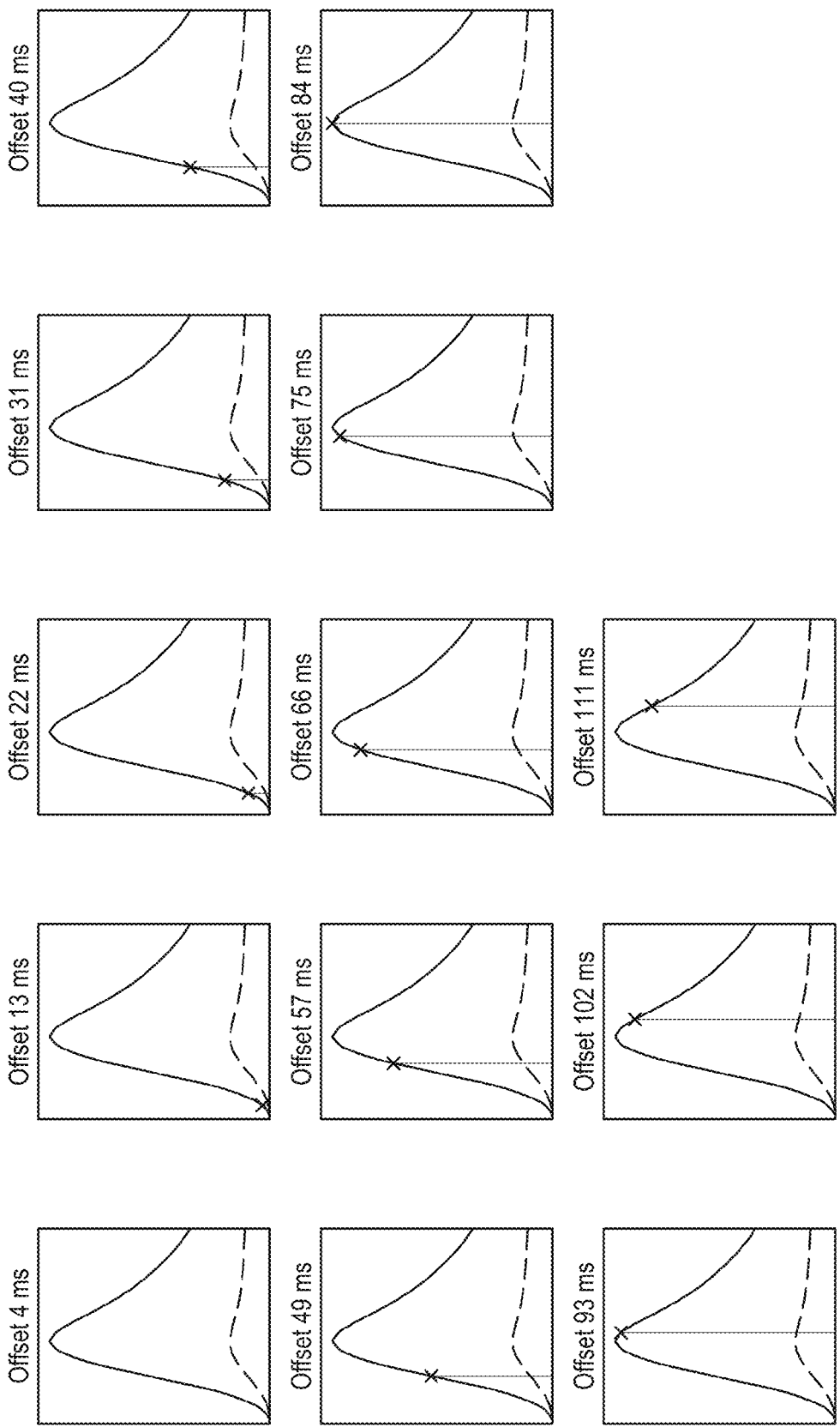
FIG. 8B is a set of graphs of discrete time-domain delayed points in time as used to build a change in temperature per change in time curve versus time curve.

FIG. 8B is a set of graphs of discrete time-domain delayed points in time as used to build a change in temperature per change in time curve versus time curve. Each individual graph in FIG. 8B represents a discrete point of change of temperature per change in time disposed on a true curve of change in temperature per change in time versus time for low and high concentrations of nanoparticles. Each graph is offset in time by 9 ms. As shown, a 9 ms offset allows for an accurate construction or approximation of the true curve. As shown, the ideal detection time or peak is at about 84 ms between light emission and thermal signal capture). Flow assays can be tested at this time to yield the most dependable peaks over noise or background levels and give the greatest peak for even a low concentration of nanoparticles. Testing in the above manner allows for detection of a low concentration (e.g., a mild or early stage illness) over noise or background levels. After determining the ideal detection time, a user can program the system or the system can automatically test subsequent samples with this offset time-domain delay to yield the most sensitive and accurate results.

In an embodiment, a user can run enough iterations to determine both the ideal detection time and the noise level, above which accurate detection may not be possible. The noise level can be where LFA's having low concentrations, high concentrations, or no concentrations of nanoparticles exhibit levels of baseline heat radiance which are indistinguishable from one another (shown at the right side of the FIGS. 3B and 8A. Such a point of noise can be determined by examining where the respective change in temperature per change in time versus time curves for a high concentration sample and a low concentration sample converge. This point shows the detection limit (e.g., point below which test data should not be trusted as indicating a positive result). In some embodiments, determining the presence of an analyte in a sample based on a plurality of thermal signals includes capturing an analyte test signal at the ideal detection time and determining if the thermal signature (e.g., temperature characteristic, such as temperature, change in temperature at a given time, or change in temperature per change in time at a given time) is above the detection limit indicated by the determined noise level.

The methods and systems described herein can be used to determine if a test has functioned properly by examining the thermal signatures at or near the control line in a similar or identical manner as described herein with respect to the test line.

The reader will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. The reader will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. The reader will recognize that optical aspects of implementations will typically employ optically-oriented hardware, software, and or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, the reader will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

In a general sense, the various embodiments described herein can be implemented, individually and/or collectively, by various types of electro-mechanical systems having a wide range of electrical components such as hardware, software, firmware, or virtually any combination thereof; and a wide range of components that may impart mechanical force or motion such as rigid bodies, spring or torsional bodies, hydraulics, and electro-magnetically actuated devices, or virtually any combination thereof. Consequently, as used herein "electro-mechanical system" includes, but is not limited to, electrical circuitry operably coupled with a transducer (e.g., an actuator, a motor, a piezoelectric crystal, etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), electrical circuitry forming a communications device (e.g., a modem, communications switch, or optical-electrical equipment), and any non-electrical analog thereto, such as optical or other analogs. Those skilled in the art will also appreciate that examples of electro-mechanical systems include but are not limited to a variety of consumer electronics systems, as well as other systems such as motorized transport systems, factory automation systems, security systems, and communication/computing systems. Those skilled in the art will recognize that electro-mechanical as used herein is not necessarily limited to a system that has both electrical and mechanical actuation except as context may dictate otherwise.

In a general sense, the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). The subject matter described herein may be implemented in an analog or digital fashion or some combination thereof.

The herein described components (e.g., steps), devices, and objects and the discussion accompanying them are used as examples for the sake of conceptual clarity. Consequently, as used herein, the specific exemplars set forth and the accompanying discussion are intended to be representative of their more general classes. In general, use of any specific exemplar herein is also intended to be representative of its class, and the non-inclusion of such specific components (e.g., steps), devices, and objects herein should not be taken as indicating that limitation is desired.

With respect to the use of substantially any plural and/or singular terms herein, the reader can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components and/or wirelessly interactable and/or wirelessly interacting components and/or logically interacting and/or logically interactable components.

In some instances, one or more components may be referred to herein as "configured to." The reader will recognize that "configured to" can generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims. In general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an"

limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense the convention (e.g., "a system having at least one of A, B, or C" would include but not be limited to systems that have A alone, B alone, C alone, A and B together, A and C together, B and C together, and/or A, B, and C together, etc.). Virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

With respect to the appended claims, the recited operations therein may generally be performed in any order. Examples of such alternate orderings may include overlapping, interleaved, interrupted, reordered, incremental, preparatory, supplemental, simultaneous, reverse, or other variant orderings, unless context dictates otherwise. With respect to context, even terms like "responsive to," "related to," or other past-tense adjectives are generally not intended to exclude such variants, unless context dictates otherwise.

While various aspects and embodiments have been disclosed herein, the various aspects and embodiments disclosed herein are for purposes of illustration and are not intended to be limiting, with the true scope and spirit being indicated by the following claims.

What is claimed is:

1. A system for detecting a presence of an analyte in a sample disposed in a flow assay having optically-absorbing indicator particles therein, the system comprising:
   a light source positioned and configured to irradiate at least a portion of the flow assay and the optically-absorbing indicator particles therein;
   a photothermal spectroscopy assay reader configured to capture a plurality of thermal signals of the flow assay including the optically-absorbing indicator particles; and
   a control system including control electrical circuitry operably coupled to the light source and the photothermal spectroscopy assay reader, the control electrical circuitry configured to synchronize operation of the light source and the photothermal spectroscopy assay reader at progressively offset time intervals and generate rate of change in temperature as a function of time data for a plurality of time data points at least partially based on a plurality of temperature readings each taken at one of the progressive offset time intervals.

2. The system of claim 1, further including:
   a support structure supporting the light source, the photothermal spectroscopy assay reader, and a carriage; and
   wherein the carriage is configured to retain the flow assay in a work position to allow for irradiation of the optically-absorbing indicator particles in a portion of the flow assay and for the portion of the flow assay to be within a field of view of the photothermal spectroscopy assay reader so that the plurality of thermal signals of the portion of the flow assay can be captured.

3. The system of claim 1, wherein optically-absorbing indicator particles include gold nanoparticles.

4. The system of claim 1, wherein the light source includes a laser.

5. The system of claim 1, wherein the photothermal spectroscopy assay reader includes an infrared camera.

6. The system of claim 1, wherein:
   the control electrical circuitry is configured to send a plurality of light emission signals to the light source and a plurality of capture signals to the photothermal spectroscopy assay reader;
   the light source is configured to emit a plurality of pulses of light responsive to receiving one or more of the plurality of light emission signals from the control electrical circuitry; and
   the photothermal spectroscopy assay reader is configured to capture one or more of the plurality of thermal signals of the flow assay responsive to receiving one or more of the plurality of capture signals from the control electrical circuitry.

7. The system of claim 6, wherein:
   the light source includes an emission trigger operably coupled thereto, the emission trigger configured to cause emission of one or more of a plurality of pulses of light from the light source responsive to receiving the one or more of the plurality of light emission signals; and
   the photothermal spectroscopy assay reader includes a capture trigger operably coupled thereto, the capture trigger configured to cause the photothermal spectroscopy assay reader to capture one or more of the plurality of thermal signals responsive to receiving the one or more of the plurality of capture signals.

8. The system of claim 6, wherein the control electrical circuitry is configured to progressively offset, in a time-domain, sending the one or more of the plurality of capture signals by smaller time intervals from each of the plurality of light emission signals.

9. The system of claim 6, wherein the control electrical circuitry is configured to progressively offset, in a time-domain, sending the one or more of the plurality of capture signals by larger time intervals from each of the plurality of light emission signals.

10. The system of claim 1, wherein:
    the control system includes:
       an emission trigger operably coupled to the light source, the emission trigger configured to cause emission of a plurality of pulses of light from the light source responsive to receiving a plurality of light emission signals from the control electrical circuitry;
       a capture trigger operably coupled to the photothermal spectroscopy assay reader, the capture trigger configured to cause the photothermal spectroscopy assay reader to capture one or more of a plurality of thermal signals responsive to receiving one or more of a plurality of capture signals; and the control electrical circuitry is configured to send:
- a plurality of light emission signals to the emission trigger each of which is effective to trigger emission of one or more of a plurality of pulses of light from the light source; and
- a plurality of capture signals to the capture trigger each of which is effective to cause the photothermal spectroscopy assay reader to capture one or more of the plurality of thermal signals; and the control electrical circuitry includes a time-delay gate configured to offset sending one or more of the plurality of capture signals corresponding to each of the plurality of light emission signals in progressively larger offset time-domain intervals in order to capture a plurality of sequentially time-delayed thermal signals of the flow assay.

11. The system of claim 10, wherein the control electrical circuitry includes a signal relay configured to send one or more of the plurality of capture signals and one or more of the plurality of light emission signals.

12. The system of claim 10 wherein:
the control system includes memory operably coupled to the control electrical circuitry; and
the photothermal spectroscopy assay reader is configured to send each of the plurality of thermal signals to the memory for storage therein.

13. The system of claim 12, further including:
a user interface operably coupled to the control system, the user interface configured to display the plurality of thermal signals to a user, enable input of user instructions, enable input of operational programs, or output thermal signal data.

14. The system of claim 10 wherein the photothermal spectroscopy assay reader includes detector control electrical circuitry configured to relay each of the plurality of thermal signals to the control system.

15. The system of claim 14, wherein the light source includes light source control electrical circuitry configured to regulate and control one or more of intensity, duration, width, or average color spectrum of light emitted from the light source responsive to receiving one of the plurality of light emission signals.

16. The system of claim 1 wherein:
the control system includes detector control electrical circuitry operably coupled to the photothermal spectroscopy assay reader and the control electrical circuitry, the detector control electrical circuitry configured to generate a plurality of synchronization signals each of which reports a time of capture of one or more of the plurality of thermal signals;
the control electrical circuitry is configured to send a plurality of light emission signals to the light source responsive to receiving each of the plurality of synchronization signals; and
the light source is configured to emit a plurality of pulses of light responsive to receiving one or more of the plurality of light emission signals from the control electrical circuitry.

17. The system of claim 16, wherein the control electrical circuitry is configured to progressively offset, in a time-domain, sending one of the plurality of light emission signals by larger time intervals from each successive synchronization signal of the plurality of synchronization signals.

18. The system of claim 16, wherein:
the detector control electrical circuitry includes a synchronization signal unit configured to send each of the plurality of synchronization signals to the control electrical circuitry;
the control electrical circuitry includes a signal relay configured to receive each of the plurality of synchronization signals and responsive thereto, send one or more of the plurality of light emission signals to the light source; and
the light source includes an emission trigger operably coupled thereto, the emission trigger configured to cause emission of a plurality of pulses of light from the light source responsive to receiving the one or more of the plurality of light emission signals.

19. The system of claim 18, wherein:
the photothermal spectroscopy assay reader is configured to capture a series of thermal signals at a repeating time-domain interval;
the synchronization signal unit is configured to send a synchronization signal to the control electrical circuitry at the repeating time-domain interval corresponding to each thermal signal of the series of thermal signals; and
the control electrical circuitry includes a time-delay gate operably coupled to the signal relay and configured to offset sending each light emission signal corresponding to each successive synchronization signal of the series of synchronization signals in progressively offset time-domain intervals in order to capture a series of thermal signals of the flow assay having progressively offset time-domain delays therebetween.

20. The system of claim 19, wherein the detector control electrical circuitry includes the synchronization signal unit configured to control the repeating time-domain interval between each of the plurality of thermal signals.

21. The system of claim 19, wherein the control system includes memory operably coupled to the control electrical circuitry, the memory configured to store one or more timing programs and one or more of the plurality of thermal signals therein.

22. The system of claim 19, further including:
a user interface operably coupled to the control system, the user interface configured to display one or more of the plurality of thermal signals to a user, enable input user instructions, enable input timing programs, or output thermal signal data.

23. A method of detecting a presence of an analyte in a sample, the method comprising:
providing a flow assay including a plurality of optically-absorbing indicator particles therein to a carriage of a detection apparatus;
initiating operation of a detection apparatus including,
a light source; and
a photothermal spectroscopy assay reader configured to capture a plurality of thermal signals of the flow assay including the plurality of optically-absorbing indicator particles therein;
emitting a plurality of pulses of light from the light source onto at least a portion of the flow assay;
substantially synchronizing capture of a plurality of thermal signals in progressively offset time-domain intervals, the plurality of thermal signals being of the at least a portion of the flow assay irradiated with the plurality of pulses of light;
capturing one or more of the plurality of thermal signals of the at least a portion of the flow assay irradiated with the plurality of pulses of light;

generating rate of change in temperature as a function of time data for a plurality of time data points at least partially based on a plurality of temperature readings each taken at one of the progressive offset time intervals; and determining the presence of the analyte in the sample based at least partially on the plurality of thermal signals.

24. The method of claim 23, wherein:
the plurality of pulses of light includes a series of pulses of light; and
capturing one or more of the plurality of thermal signals includes capturing a series of thermal signals at a progressively smaller offset time-domain interval from each successive pulse of light of the series of pulses of light.

25. The method of claim 24, further including reducing the offset time-domain interval by 20 milliseconds or less upon each successive pulse of light of the series of pulses of light.

26. The method of claim 25, further including reducing the offset time-domain interval by 10 milliseconds or more upon each successive pulse of light of the series of pulses of light.

27. The method of claim 23, wherein:
the plurality of pulses of light includes a series of pulses of light; and
capturing one or more of the plurality of thermal signals includes capturing each thermal signal of a series of thermal signals at a progressively larger offset time-domain interval from each successive pulse of light of the series of pulses of light.

28. The method of claim 27, further including increasing the offset time-domain interval by 3 milliseconds or more upon each successive pulse of light of the series of pulses of light.

29. The method of claim 23, further including:
determining a temperature of the at least a portion of the flow assay in each of the plurality of thermal signals;
constructing a data set of the rate of change in temperature as a function of time data at least partially based on the plurality of thermal signals; and
determining an ideal detection time by identifying a capture time corresponding to a greatest value of rate of change in temperature as a function of time from the data set.

30. The method of claim 29, wherein determining the presence of an analyte in a sample based at least partially on the plurality of thermal signals includes capturing an analyte test signal with the photothermal spectroscopy assay reader at the ideal detection time and determining if a thermal signature in the analyte test signal is above a detection limit.

31. The method of claim 23, wherein:
the detection apparatus further includes control electrical circuitry operably coupled to the light source and the photothermal spectroscopy assay reader; and
substantially synchronizing capture of a plurality of thermal signals in progressively offset time-domain intervals, the plurality of thermal signals of the at least a portion of the flow assay irradiated with the plurality of pulses of light includes,
sending a plurality of light emission signals from the control electrical circuitry to the light source, each of the plurality of light emission signals effective to trigger at least one pulse of light from the light source responsive thereto; and
sending a plurality of capture signals from the control electrical circuitry to the photothermal spectroscopy assay reader at a progressively offset time-domain delay between each successive light emission signal of the plurality of light emission signals and a capture signal corresponding thereto, wherein each of the plurality of capture signals is effective to cause the photothermal spectroscopy assay reader to capture a thermal signal of the portion of the flow assay responsive thereto.

32. The method of claim 31 further including:
wherein the light source includes a light source control electrical circuitry having an emission trigger configured to cause emission of one or more of a plurality of pulses of light from the light source responsive to receiving the one or more of the plurality of light emission signals;
wherein the photothermal spectroscopy assay reader includes detector control electrical circuitry having a capture trigger configured to cause the photothermal spectroscopy assay reader to capture one or more of the plurality of thermal signals responsive to receiving the one or more of the plurality of capture signals; and
receiving, with the emission trigger, each of the plurality of light emission signals; and
receiving, with the capture trigger, each of the plurality of capture signals.

33. The method of claim 32, wherein capturing one or more of the plurality of thermal signals of the at least a portion of the flow assay irradiated with the plurality of pulses of light includes capturing each thermal signal of a series of thermal signals at a progressively larger offset time-domain interval from each successive pulse of a series of pulses of light.

34. The method of claim 32 further including increasing the offset time-domain interval between each successive light emission signal and corresponding capture signal by 3 or more milliseconds; and
wherein sending a plurality of capture signals from the control electrical circuitry to the photothermal spectroscopy assay reader at a progressively offset time-delay between each subsequent light emission signal and corresponding capture signal includes sending each capture signal of the plurality of capture signals at an offset time-domain interval of at least about 110 milliseconds.

35. The method of claim 23, wherein:
the detection apparatus includes a control system having control electrical circuitry operably coupled to the light source and the photothermal spectroscopy assay reader; and
substantially synchronizing capture of a plurality of thermal signals in progressively offset time-domain intervals, the plurality of thermal signals of the at least a portion of the flow assay irradiated with the plurality of pulses of light includes,
sending a plurality of synchronization signals from the photothermal spectroscopy assay reader to the control electrical circuitry, each of the plurality of synchronization signals indicating a capture time of a corresponding thermal signal;
responsive to the each of the plurality of synchronization signals, sending one or more light emission signals from the control electrical circuitry to the light source, each of the plurality of light emission signals sent at a progressively offset time-domain interval from the corresponding synchronization signal and effective to trigger emission of a light pulse from the light source.

36. The method of claim 35, wherein each of the plurality of synchronization signals is approximately equally spaced by time-domain intervals of at least about 110milliseconds.

37. The method of claim 35 wherein the control electrical circuitry includes a time-delay gate configured to offset sending each of the one or more of light emission signals corresponding to each of the plurality synchronization signals in progressively larger time-domain intervals in order to capture sequentially time-delayed thermal signals of the flow assay.

38. The method of claim 35 further including increasing the offset time-domain interval between each successive one of the one or more light emission signals and corresponding capture signal by 3 milliseconds or more.

39. The method of claim 35 wherein the control electrical circuitry includes a time-delay gate configured to offset sending each of the one or more light emission signals corresponding to each of the plurality of synchronization signals in progressively smaller time-domain intervals in order to capture sequentially time-delayed thermal signals of the flow assay.

40. The method of claim 35, further including decreasing the offset time-domain interval between each successive one of the one or more light emission signals and corresponding capture signal by 3 or more milliseconds.

41. The method of claim 35, further including:
determining a temperature of the at least a portion of the flow assay in each of the plurality of thermal signals;
constructing a data set of rate of change in temperature as a function of time data based on the plurality of thermal signals; and
determining an ideal detection time by identifying a capture time corresponding to a greatest value of rate of change in temperature as a function of time from the data set.

42. The method of claim 41, wherein determining the presence of an analyte in a sample based at least partially on the plurality of thermal signals includes capturing an analyte test signal with the photothermal spectroscopy assay reader at the ideal detection time and determining if a thermal signature in the analyte test signal is above a detection limit.

43. The method of claim 35:
wherein the control system includes:
light source control electrical circuitry operably coupled to the control electrical circuitry and the light source, the light source control electrical circuitry having an emission trigger configured to cause emission of one or more of the plurality of pulses of light from the light source responsive to receiving the one or more of the plurality of light emission signals;
a synchronization signal unit operably coupled to the control electrical circuitry and configured to send a plurality of synchronization signals to the control electrical circuitry;
a signal relay operably coupled to the control electrical circuitry and the synchronization signal unit; and
receiving, with the signal relay, each of the plurality of synchronization signals and responsive thereto sending one or more of the plurality of light emission signals to the light source; and
receiving, with the emission trigger, each of the plurality of light emission signals.

44. A system for detecting an analyte in a sample disposed on a flow assay having optically-absorbing indicator particles therein, the system comprising:
a laser light source configured to emit laser light;
an infrared camera configured to capture a plurality of thermal signals of the flow assay including the optically-absorbing indicator particles;
a control system having control electrical circuitry operably coupled to the laser light source and the infrared camera, the control system including,
detector control electrical circuitry operably coupled to the control electrical circuitry and the infrared camera;
light source control electrical circuitry operably coupled to the control electrical circuitry and the laser light source;
a signal relay operably coupled the control electrical circuitry, the laser light source and the detector control electrical circuitry, the signal relay configured to send a plurality of light emission signals to the light source control electrical circuitry each of which is effective to cause the laser light source to emit a pulse of laser light, the signal relay further configured to send a plurality of capture signals to the infrared camera to capture a plurality of thermal signals of the flow assay at progressively offset time-domain intervals upon each successive one of the pulses of laser light emitted the laser light source, and
memory configured to store one or more of the plurality of thermal signals therein;
wherein the control electrical circuitry is configured to generate rate of change in temperature as a function of time data for a plurality of time data points at least partially based on a plurality of temperature readings each taken at one of the progressive offset time intervals;
a support structure supporting the laser light source, the infrared camera, and a carriage, the carriage being configured to retain the flow assay in a work position that allows for laser light emitted from the laser light source on the flow assay to be within a field of view of the infrared camera.

45. The system of claim 44, wherein the carriage is configured to repeatably retain one or more flow assays in a work position to allow for irradiation of the optically-absorbing indicator particles and for the infrared camera to capture the plurality of thermal signals of one or more flow assays and optically-absorbing indicator particles therein.

46. The system of claim 44, wherein the control electrical circuitry includes a time-delay gate configured to progressively offset sending the capture signal to the infrared camera by the progressively offset time-domain intervals.

47. The system of claim 44, wherein the control system includes a user interface through which a sample type is selected, and wherein the control electrical circuitry is configured to determine one or more offset time-domain intervals based on the selected sample type.

48. The system of claim 47, wherein:
the memory includes one or more timing programs stored thereon; and
the control electrical circuitry includes a comparative analysis circuit configured to correlate the selected sample type with one or more timing programs in the memory and execute the correlated one or more timing programs responsive thereto.

\* \* \* \* \*